(12) United States Patent
Kaminski et al.

(10) Patent No.: US 10,896,740 B2
(45) Date of Patent: Jan. 19, 2021

(54) 52-GENE SIGNATURE IN PERIPHERAL BLOOD IDENTIFIES A GENOMIC PROFILE ASSOCIATED WITH INCREASED RISK OF MORTALITY AND POOR DISEASE OUTCOMES IN IDIOPATHIC PULMONARY FIBROSIS

(71) Applicant: Yale University, New Haven, CT (US)

(72) Inventors: Naftali Kaminski, New Haven, CT (US); Jose D. Herazo-Maya, North Haven, CT (US)

(73) Assignee: Yale University, New Haven, CT (US)

( * ) Notice: Subject to any disclaimer, the term of this patent is extended or adjusted under 35 U.S.C. 154(b) by 540 days.

(21) Appl. No.: 15/727,482

(22) Filed: Oct. 6, 2017

(65) Prior Publication Data
US 2018/0101642 A1 Apr. 12, 2018

Related U.S. Application Data

(60) Provisional application No. 62/405,799, filed on Oct. 7, 2016.

(51) Int. Cl.
| | |
|---|---|
| *G16B 20/00* | (2019.01) |
| *C12Q 1/6883* | (2018.01) |
| *C40B 30/06* | (2006.01) |
| *C12N 15/10* | (2006.01) |
| *G16B 25/00* | (2019.01) |

(52) U.S. Cl.
CPC .......... *G16B 20/00* (2019.02); *C12N 15/1086* (2013.01); *C12Q 1/6883* (2013.01); *C40B 30/06* (2013.01); *G16B 25/00* (2019.02); *C12Q 2600/118* (2013.01); *C12Q 2600/158* (2013.01)

(58) Field of Classification Search
CPC .... G16B 20/00; G16B 25/00; C12N 15/1086; C12Q 1/6883; C40B 30/06
USPC .......................................................... 702/19
See application file for complete search history.

(56) References Cited

PUBLICATIONS

Gilani et al., CD28 down-regulation on circulating CD4 T-cells is associated with poor prognoses of patients with idiopathic pulmonary fibrosis. PLoS One. Jan. 29, 2010;5(1):e8959. doi: 10.1371/journal.pone.0008959.
Greene et al., Serum surfactant proteins-A and -D as biomarkers in idiopathic pulmonary fibrosis. Eur Respir J. Mar. 2002;19(3):439-46.
Herazo-Maya et al., Peripheral blood mononuclear cell gene expression profiles predict poor outcome in idiopathic pulmonary fibrosis. Sci Transl Med. Oct. 2, 2013;5(205):205ra136. doi: 10.1126/scitranslmed.3005964.
Herazo-Maya et al., Validation of a 52-gene risk profile for outcome prediction in patients with idiopathic pulmonary fibrosis: an international, multicentre, cohort study. Lancet Respir Med. Nov. 2017;5(11):857-868. doi: 10.1016/S2213-2600(17)30349-1. Epub Sep. 21, 2017.
Herazo-Maya et al., Supplementary Information for Validation of a 52-gene risk profile for outcome prediction in patients with idiopathic pulmonary fibrosis: an international, multicentre, cohort study. Lancet Respir Med. Nov. 2017;5(11):857-868. doi: 10.1016/S2213-2600(17)30349-1. Epub Sep. 21, 2017.
Korthagen et al., Serum and BALF YKL-40 levels are predictors of survival in idiopathic pulmonary fibrosis. Respir Med. Jan. 2011;105(1):106-13. doi: 10.1016/j.rmed.2010.09.012.
Ley et al., A multidimensional index and staging system for idiopathic pulmonary fibrosis. Ann Intern Med. May 15, 2012;156(10):684-91. doi: 10.7326/0003-4819-156-10-201205150-00004.
Ley et al., Molecular biomarkers in idiopathic pulmonary fibrosis. Am J Physiol Lung Cell Mol Physiol. Nov. 1, 2014; 307(9):L681—L691.
Moeller et al., Circulating fibrocytes are an indicator of poor prognosis in idiopathic pulmonary fibrosis. Am J Respir Crit Care Med. Apr. 1, 2009;179(7):588-94. doi: 10.1164/rccm.200810-1534OC. Epub Jan. 16, 2009.
Noth et al., Genetic variants associated with idiopathic pulmonary fibrosis susceptibility and mortality: a genome-wide association study. Lancet Respir Med. Jun. 2013;1(4):309-317. doi: 10.1016/S2213-2600(13)70045-6. Epub Apr. 17, 2013.
O'Dwyer et al., The Toll-like receptor 3 L412F polymorphism and disease progression in idiopathic pulmonary fibrosis. Am J Respir Crit Care Med. Dec. 15, 2013;188(12):1442-50. doi: 10.1164/rccm.201304-0760OC.
Peljto et al., Association Between the MUC5B Promoter Polymorphism and Survival in Patients With Idiopathic Pulmonary Fibrosis. JAMA. Jun. 5, 2013; 309(21): 2232-2239.
Prasse et al., Serum CC-chemokine ligand 18 concentration predicts outcome in idiopathic pulmonary fibrosis. Am J Respir Crit Care Med. Apr. 15, 2009;179(8):717-23. doi: 10.1164/rccm.200808-1201OC. Epub Jan. 29, 2009.
Reilkoff et al., Semaphorin 7a+ regulatory T cells are associated with progressive idiopathic pulmonary fibrosis and are implicated in transforming growth factor-β1-induced pulmonary fibrosis. Am J Respir Crit Care Med. Jan. 15, 2013;187(2):180-8. doi: 10.1164/rccm.201206-1109OC. Epub Dec. 6, 2012.
Richards et al., Peripheral blood proteins predict mortality in idiopathic pulmonary fibrosis. Am J Respir Crit Care Med. Jan. 1, 2012;185(1):67-76. doi: 10.1164/rccm.201101-0058OC.
Rosas et al., MMP1 and MMP7 as potential peripheral blood biomarkers in idiopathic pulmonary fibrosis. PLoS Med. Apr. 29, 2008;5(4):e93. doi: 10.1371/journal.pmed.0050093.
Ryu et al., Extracellular Mitochondrial DNA Is Generated by Fibroblasts and Predicts Death in Idiopathic Pulmonary Fibrosis. Am J Respir Crit Care Med. Dec. 15, 2017;196(12):1571-1581. doi: 10.1164/rccm.201612-2480OC.

(Continued)

*Primary Examiner* — Jerry Lin
(74) *Attorney, Agent, or Firm* — Wolf, Greenfield & Sacks, P.C.

(57) ABSTRACT

The clinical course of idiopathic pulmonary fibrosis (IPF) is difficult to predict. Described herein is a peripheral blood 52-gene expression signature useful to improve outcome prediction in IPF.

20 Claims, 9 Drawing Sheets
(8 of 9 Drawing Sheet(s) Filed in Color)

(56) References Cited

PUBLICATIONS

Tarjiri et al., Serum level of periostin can predict long-term outcome of idiopathic pulmonary fibrosis. Respir Investig. Mar. 2015;53(2):73-81. doi: 10.1016/j.resinv.2014.12.003. Epub Jan. 19, 2015.

Tzouvelekis et al., Validation of the prognostic value of MMP-7 in idiopathic pulmonary fibrosis. Respirology. Apr. 2017;22(3):486-493. doi: 10.1111/resp.12920. Epub Oct. 19, 2016.

Vuga et al., C-X-C motif chemokine 13 (CXCL13) is a prognostic biomarker of idiopathic pulmonary fibrosis. Am J Respir Crit Care Med. Apr. 15, 2014;189(8):966-74. doi: 10.1164/rccm.201309-1592OC.

Yokoyama et al., Prognostic value of circulating KL-6 in idiopathic pulmonary fibrosis. Respirology. Mar. 2006;11(2):164-8.

52-GENE SIGNATURE IN PERIPHERAL BLOOD IDENTIFIES A GENOMIC PROFILE ASSOCIATED WITH INCREASED RISK OF MORTALITY AND POOR DISEASE OUTCOMES IN IDIOPATHIC PULMONARY FIBROSIS

RELATED APPLICATIONS

This application claims the benefit of the filing date under 35 U.S.C. § 119 of U.S. Provisional Application No. 62/405,799, filed Oct. 7, 2016, the entire contents of which are incorporated by reference herein.

FEDERALLY SPONSORED RESEARCH

This invention was made with government support under grant numbers U01 HL112707, R01 HL127349, U01 HL108642, and UH3 HL123886 awarded by the National Institutes of Health. The government has certain rights in the invention.

BACKGROUND

Idiopathic pulmonary fibrosis (IPF) is a progressive and highly lethal interstitial lung disease of unknown etiology. The median survival without transplant is approximately three to four years[1]. The natural history of the disease is highly variable and unpredictable; some patients demonstrate long term clinical stability and others experience a more rapid disease course[2]. Although clinical parameters allow staging of patients, they do not predict outcome accurately[3].

SUMMARY

Described herein is work that demonstrates that a score based on a 52-gene expression signature (whose members are described herein) accurately classifies IPF patients into two distinct risk profile groups and improves outcome prediction of clinical staging, including in independent IPF cohorts. Temporal changes in this 52-gene signature score associate with changes in forced vital capacity (FVC). Substantial (≥10%) bidirectional changes accurately predict subsequent transplant-free survival.

The 52-gene expression signature was measured in peripheral blood from 425 IPF patients prospectively followed at six academic institutions. The Scoring Algorithm of Molecular Subphenotypes (SAMS) method was used to calculate a risk score based on the values of 52 genes. Competing risk and Cox proportional hazard (CoxPH) models were used for outcome prediction. Gene expression trends over time were analyzed using linear mixed-effect models. The association between bidirectional changes in SAMS scores and survival was obtained using a Cox proportional-hazards model.

Described herein is a method of assessing a sample obtained from an individual for each of 52 genes. In one embodiment, the method comprises: (a) measuring expression level (e.g., gene transcript count) of each of the 52 genes listed in Table 7 in a sample (such as blood, peripheral blood mononuclear cells; e.g., RNA obtained from blood or peripheral blood mononuclear cells) from the individual (such as an individual with IPF), thereby producing an expression level for each of the genes; (b) comparing the expression level of each gene in the sample with a gene-specific standard that is, for example, the geometric mean of a reference population (e.g., a group of individuals known to have IPF), thereby producing a normalized expression level for each gene in the sample; (c) determining (i) if the normalized expression level of each of PLBD1, TPST1, C19orf59 (MCEMP1), IL1R2, HP, FLT3, and S100A12 is greater than (up, relative to) the gene-specific standard, wherein if the normalized expression level of a gene is greater than the gene-specific standard, the gene is an upregulated gene and (ii) if the normalized expression level of each of LCK, CAMK2D, NUP43, SLAMF7, LRRC39, ICOS, CD47, LBH, SH2D1A, CNOT6L, METTL8, ETS1, C2orf27A, P2RY10, TRAT1, BTN3A1, LARP4, TC2N, GPR183, MORC4, STAT4, LPAR6, C7orf58 (CPED1), DOCK10, ARHGAP5, HLA-DPA1, BIRC3, GPR174, CD28, UTRN, CD2, HLA-DPB1, ARL4C, BTN3A3, CXCR6, DYNC2LI1, BTN3A2, ITK, SNHG1, CD96, GBP4, S1PR1, NAP1L2, KLF12, and IL7R is less than (down, relative to) the gene-specific standard, wherein if the normalized expression level of a gene is less than the gene-specific standard, the gene is a downregulated gene; (d) calculating (i) the proportion of upregulated genes in the sample (the number of genes, out of 7, that have expression levels greater than the gene-specific standard), thereby producing a proportion of upregulated genes and (ii) the proportion of downregulated genes in the sample (the number of genes, out of 45, that have expression levels less than the gene-specific standard), thereby producing a proportion of downregulated genes; (e) summing (adding) the normalized expression levels of the upregulated genes and multiplying the resulting sum by the proportion of upregulated genes of (d)(i), thereby producing an up score; (f) summing (adding) the normalized expression levels of the downregulated genes and multiplying the resulting sum by the proportion of downregulated genes of (d)(ii), thereby producing a down score; and (g) comparing the up score to a reference up score and the down score to a reference down score.

In some embodiments, the individual (e.g., a human), has idiopathic pulmonary fibrosis (IPF), and the 52-gene signature may be used to determine the individual's risk profile. For example, if an individual's up score is greater than the reference up score and the down score is less than the reference down score, the individual is at a high (increased) risk of poor disease outcome; alternatively, if the up score is less than the reference up score and the down score is more than the reference down score, the individual is at low (decreased) risk of poor disease outcome. An individual at increased risk or likelihood of poor disease outcome is more likely to have a poor disease outcome as a result of the condition than if he/she were in the low risk group. Poor disease outcome can be, for example, earlier death, need for transplant (e.g., a lung transplant), or reduced forced vital capacity as a result of the condition.

Testing of expression of the genes can be carried out, for example, by gene transcript counting using Nanostring, polymerase chain reaction (PCR), microarray technology and RNA sequencing.

In a further embodiment, the GAP index for idiopathic pulmonary fibrosis mortality or other clinical prognostic test for IPF mortality is used in conjunction with the method described above.

In another embodiment, the expression level measurement is carried out using the Nanostring preparation station and digital analyzer.

An additional aspect of the invention includes a method of assessing disease outcome (e.g., transplant-free survival, risk of death) in an individual with idiopathic pulmonary fibrosis (IPF), the method comprising: (a) measuring expression level (e.g., gene transcript count) of each of the 52 genes listed in Table 7 in a sample (e.g., RNA from blood or peripheral blood mononuclear cells) from the individual, thereby producing an expression level for each gene in the sample; (b) comparing the expression level of each gene in the sample with a gene-specific standard that is the geometric mean of a reference population, thereby producing a normalized expression level for each gene; (c) determining (i) if the normalized expression level of each of PLBD1, TPST1, C19orf59 (MCEMP1), IL1R2, HP, FLT3, and S100A12 is greater than (up, relative to) the gene-specific standard, wherein if the normalized expression level of a gene is greater than the gene-specific standard, the gene is an upregulated gene and (ii) if the normalized expression level of each of LCK, CAMK2D, NUP43, SLAMF7, LRRC39, ICOS, CD47, LBH, SH2D1A, CNOT6L, METTL8, ETS1, C2orf27A, P2RY10, TRAT1, BTN3A1, LARP4, TC2N, GPR183, MORC4, STAT4, LPAR6, C7orf58 (CPED1), DOCK10, ARHGAP5, HLA-DPA1, BIRC3, GPR174, CD28, UTRN, CD2, HLA-DPB1, ARL4C, BTN3A3, CXCR6, DYNC2LI1, BTN3A2, ITK, SNHG1, CD96, GBP4, S1PR1, NAP1L2, KLF12, and IL7R is less than (down, relative to) the gene-specific standard, the gene is a downregulated gene; (d) calculating (i) the proportion of upregulated genes in the sample (the number of genes, out of 7, that have expression levels greater than the gene-specific standard), thereby producing a proportion of upregulated genes and (ii) the proportion of downregulated genes in the sample (the number of genes, out of 45, that have expression levels less than the gene-specific standard), thereby producing a proportion of downregulated genes; (e) summing (adding) the normalized expression levels of the upregulated genes and multiplying the resulting sum by the proportion of upregulated genes of (d)(i), thereby producing an up score; (f) summing (adding) the normalized expression levels of the downregulated genes and multiplying the resulting sum by the proportion of downregulated genes of (d)(ii), thereby producing a down score; (g) repeating steps (a) through (f) in a sample obtained from the individual at a later time, thereby producing a second up score and a second down score; (h) calculating the change in/difference between the up score of (e) and the second up score; (i) calculating the change in/difference between the down score of (f) and the second down score; and (j) determining whether the second up score is at least 10% greater than (≥10%) the up score of (e) and whether the second down score is at least 10% lower than the down score of (f), wherein, if the second up score is at least 10% greater than the up score of (e) and the second down score is at least 10% lower than the down score of (f), the individual is at high risk of poor disease outcome and if one or none of the changes in up score and in down score are less than 10%, the individual is at low risk of poor disease outcome.

In a further embodiment, the GAP index for idiopathic pulmonary fibrosis mortality or other clinical prognostic test for IPF mortality is used in conjunction with the method described above.

In other embodiments, the expression level is measured using the Nanostring preparation station and digital analyzer.

Work described herein demonstrates that a 52-gene signature in peripheral blood is able to distinguish two genomic risk profiles with significant differences in mortality and TFS. The enhancement in outcome prediction when combining high risk genomic profiles with the GAP index (G-GAP index), the association of gene expression changes over time with FVC and the survival predictive ability of these changes, indicates the value of a blood test using the 52-gene in clinical practice for risk stratification and disease monitoring in IPF.

The following is a brief description of the results. The application of SAMS to the 52-gene signature identified two molecular subphenotypes (low and high risk) of IPF patients with significant differences in mortality or transplant-free survival in all cohorts (HR 2.03-4.37). Pooled data revealed similar results for mortality (HR 2.18, 95% CI:1.53-3.09, P<0.001) or transplant-free survival (HR: 2.04, 95% CI: 1.52-2.74, P<0.001). Adding SAMS scores to the GAP clinical staging system significantly improved its outcome predictive accuracy, particularly at 30 days (13% increase in Area Under the Curve for mortality prediction and 10.6% for transplant-free survival). Per patient temporal changes in SAMS were significantly associated (P<0.01) with changes in FVC. Substantial bidirectional changes (≥10%) in scores were highly predictive of subsequent transplant-free survival.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 2A) Clustering of IPF patients based on genomic risk profiles (high vs low) derived from the 52-gene signature using SAMS in each one of the six cohorts studied. Every row represents a gene and every column represents a patient. Color scale is shown adjacent to heat maps in log-based two scale; generally, yellow denotes increase over the geometric mean of samples and purple, a decrease. (FIG. 2B) Mortality and Transplant-free survival (TFS) differs between high versus low risk profiles based on the 52-gene signature in each independent cohort. HR=hazard ratio.

(FIG. 3A) Pooled data analysis comparing high vs low risk profile patients from all cohorts. Color scale is shown adjacent to heat maps in log-based two scale. Mortality (FIG. 3B) and transplant-free survival (TFS) (FIG. 3C) differs between high vs low risk patients from all cohorts after adjusting for age, gender, FVC % and immunosuppressive therapy. Area under the curve (AUC) of time-dependent ROC analysis for mortality (FIG. 3D) and TFS (FIG. 3E) based on the GAP index alone or the G-GAP index in all patients. G-GAP=GAP and genomic. HR=hazard ratio.

(FIG. 4D) Bidirectional changes in SAMS scores (simultaneous increase in up score and decrease in down score) can be observed during disease course in IPF and are more prominent in high risk individuals (example shown in dotted black line box). (FIG. 4E) Bidirectional changes in SAMS scores are predictive of transplant-free survival (TFS). Dotted line (high risk)—

Pittsburgh cohort patients with 30-day bidirectional changes in SAMS scores ≥10%. Continuous line (low risk)—Pittsburgh cohort patients with 30-day bidirectional changes in SAMS scores <10%. Results adjusted to age, gender, FVC and immunosuppressive therapy.

Figure 5:
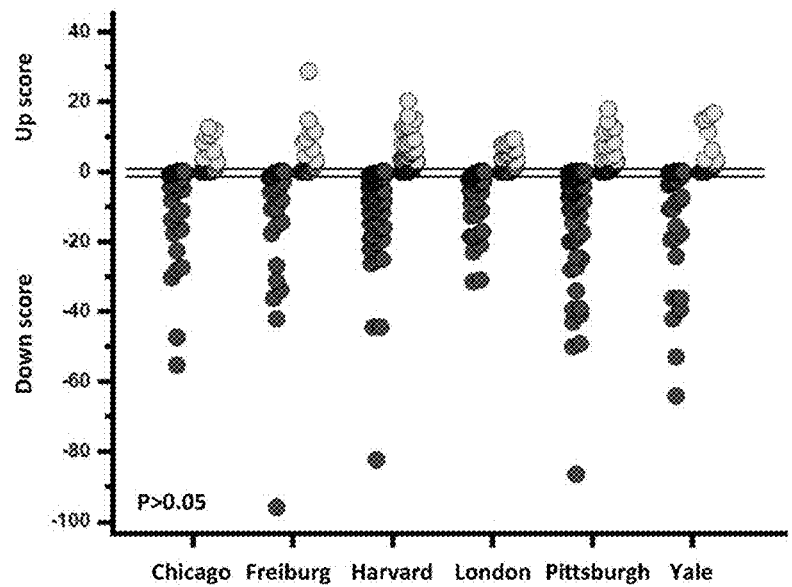

FIG. 5. SAMS scores are not significantly different between cohorts. The y axis from this graph represents the SAMS up scores (above 0) and down scores (below 0) per patient. The yellow dots represent the up scores and the purple dots represent the down scores. The continuous lines above 0 and below 0, represent the median up score and the median down score values, respectively. Up and down scores were not significantly (p<0.05) different between cohorts.

Figure 6A:
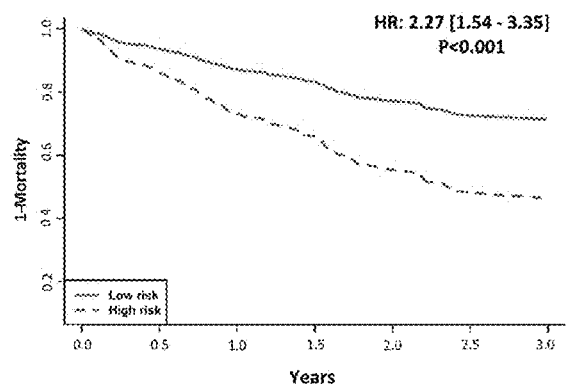
Figure 6B:
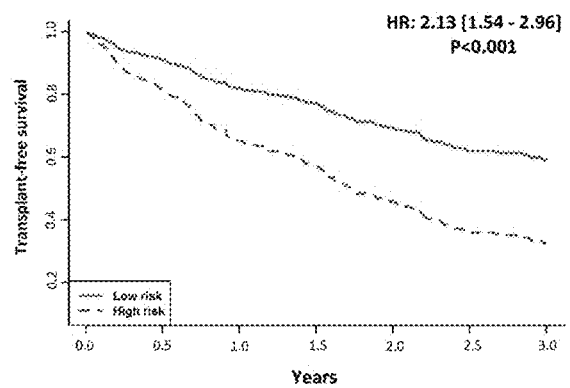

FIGS. 6A-6B. Genomic risk profiles are predictive of poor IPF outcomes in IPF patients not under immunosuppressive therapy. Mortality (FIG. 6A) and transplant-free survival (TFS) (FIG. 6B) differ from patients in all cohorts with high vs low risk genomic profiles, based on the 52-gene signature, who were not on immunosuppressive therapy at the time of blood draw. Results were adjusted to age, gender and FVC.

Figure 7A:
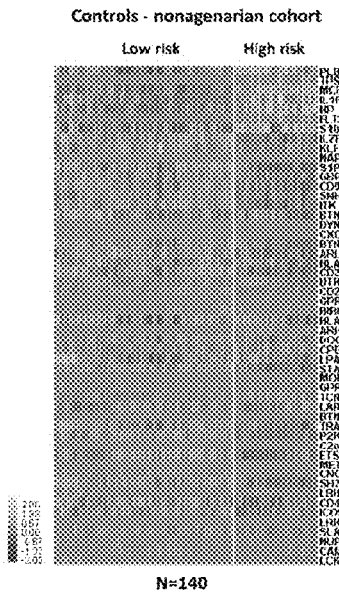
Figure 7B:
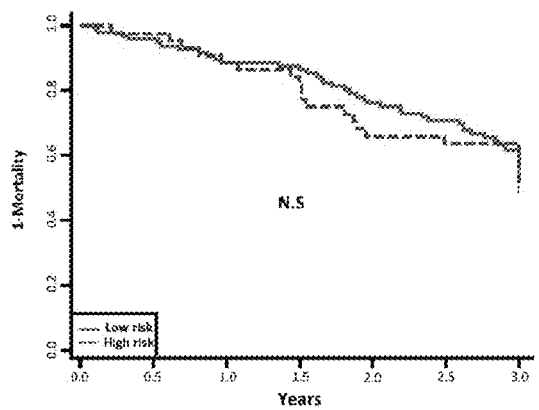

FIGS. 7A-7B. Genomic risk profiles based on the 52-gene signature are not predictive of mortality in a cohort of individuals older than 90 years of age. (FIG. 7A) Clustering of control patients based on genomic risk profiles (high vs. low) derived from the 52-gene signature using SAMS. Every row represents a gene and every column a patient. Color scale is shown adjacent to heat maps in log-based two scale; generally, yellow denotes increase over the geometric mean of samples and purple, a decrease. (FIG. 7B) Mortality does not differ significantly between high vs low risk profiles based on the 52-gene signature in the cohort of individuals older than 90 years of age.

Figure 8A:
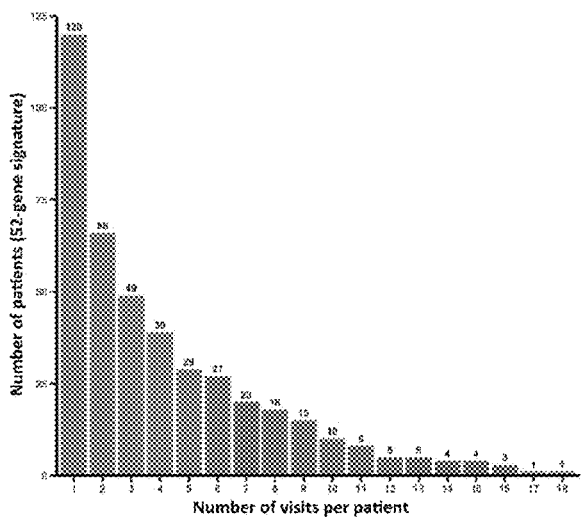
Figure 8B:
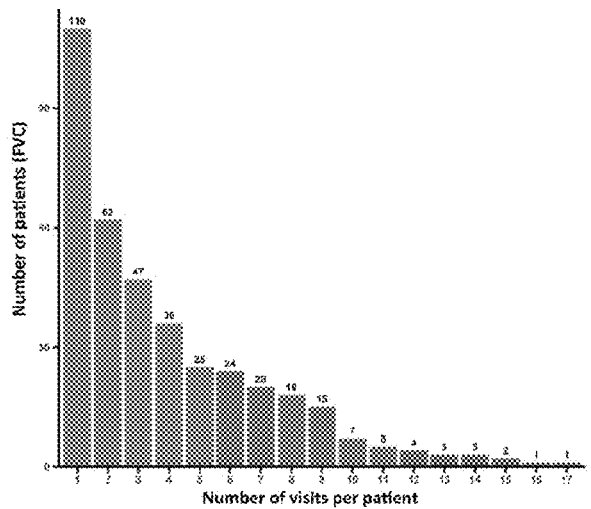

FIGS. 8A-8B. Frequency of PBMC and FVC measurements. The y-axis in the figure represents the number of 52-gene measurements in PBMC (FIG. 8A) and FVC data (FIG. 8B) collected in each follow up visit. The x axis represents the number of visits per patient. In this axis, one (1) represent the blood sample or FVC collected at baseline.

Figure 9A:
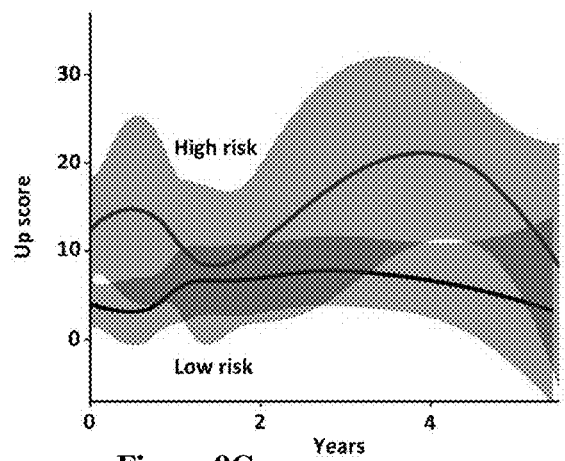
Figure 9B:
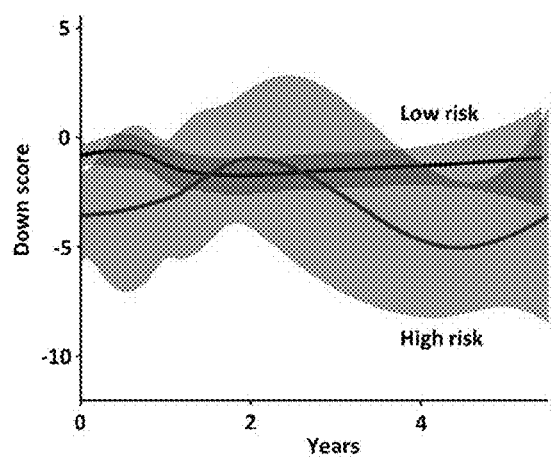
Figure 9C:
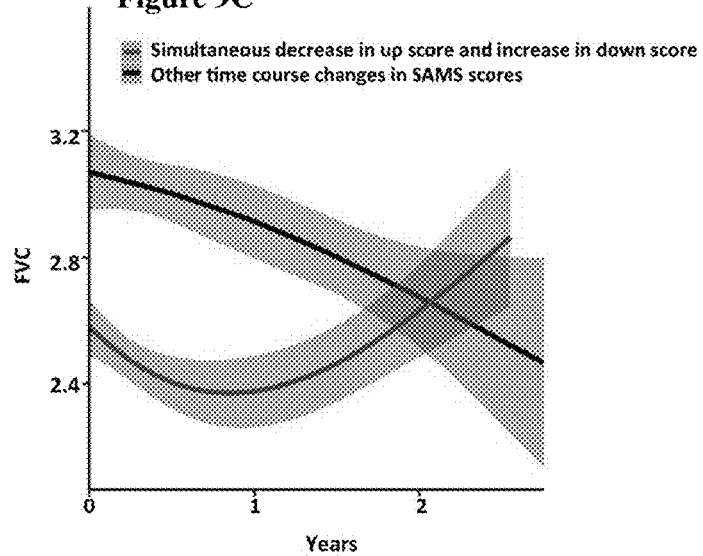

FIGS. 9A-9C. 52-gene signature trends in high risk IPF patients shift after initiation of anti-fibrotic therapy. Up (FIG. 9A) and down (FIG. 9B) scores from SAMS shift their trends over time in high (red line) vs low (black line) risk groups after initiation of anti-fibrotic therapy. (FIG. 9C) FVC trends of treated patients who had a simultaneous decrease in up score and increase in down score (black line) vs other score changes (red line). Pointwise confidence intervals are represented in purple.

DETAILED DESCRIPTION

Described herein is a 52-gene signature (Table 7) and its use in two novel genomic risk profiles relating to disease outcome.

The recognition of the variable clinical course in idiopathic pulmonary fibrosis (IPF) has led to a substantial effort to identify clinical tools and reliable peripheral blood biomarkers for risk stratification. Changes in peripheral blood proteins such as MMP7,[4,13] ICAM and interleukin 8,[4] surfactant proteins A and D,[5] mucin 1 (KL-6),[23] CCL18,[24] CHI3L1,[25] CXL13,[26] POSTN,[27] anti-hsp70 IgG antibodies,[28] and protease degradation products,[29] have been found to be predictive of poor IPF outcomes. Changes in circulating cells (CD4-positive CD28-positive T cells,[6] fibrocytes,[30] and semaphoring 7a-positive regulatory T cells[31]), gene polymorphisms (TOLLIP,[32] TLR3,[33] and MUC5B[7]), and ageing biomarkers (telomere length[8] and free mitochondrial DNA[34]) have also been associated with mortality in IPF. Although these studies strongly suggest the value of peripheral blood biomarkers for risk stratification in IPF, no marker is available for use in clinical practice because, in part, most studies did not have truly independent replication cohorts, nor did they show added value over clinical staging tools. In contrast with previous studies, the data described herein validates a 52-gene expression signature in six independent IPF cohorts and shows substantially improved accuracy when incorporated with available clinical tools.

These attributes are important because accurate outcome prediction has very practical implications for patients with IPF. Based on the lung allocation score and on their clinical characteristics, nearly all of the patients in the study would be referred for transplant evaluation, and many would be eligible for lung transplantation. However, the present data suggest that only patients with a high-risk genomic profile could require this evaluation urgently, and many might not require lung transplantation, even 3-5 years after diagnosis. Thus, incorporation of 52-gene risk profiles in the evaluation of patients with IPF might enhance the precision of lung transplantation referral—avoiding delays in transplants to those patients who need it early, and delaying those patients who might not need it. Similarly, when lung transplantation is not an option, this test could also help physicians to decide when to refer patients with IPF to palliative care, a greatly unmet need,[35] or distinguish between patients who respond to drug therapy from those patients who do not.

Additionally, most of the previous studies did not assess the change of markers over time. This assessment is important because it is unknown whether patients with IPF shift their risk profiles. The present disclosure shows that a patient's 52-gene, genomic risk profile rarely changes in the absence of antifibrotic therapy. However, when the profile does change, it is important. In untreated patients, a simultaneous increase in up score and decrease in down score reflects a subsequent increased mortality.

In patients treated with antifibrotic drugs, a simultaneous decrease in up score and increase in down score reflects stabilization or even increase in FVC. Thus, the study shows that 52-gene risk profiles at presentation are predictive of outcome and changes in a patient's genomic risk profile are informative of clinical deterioration and potential response to antifibrotic therapies.

Previous work has shown that four genes of this signature (CD28, ICOS, LCK, and ITK), which belong to the T-cell co-stimulatory signaling pathway, were correlated with the percentage of CD4-positive and CD28-positive T cells in the circulation of these patients.[6] Similarly, previous reports[36] have shown that CD28 downregulation on circulating CD4-positive T cells in patients with IPF are also associated with poor disease outcomes. These reports suggest a potential link between changes in the expression of genes in the 52-gene signature with phenotypic shifts in circulating immune cells. Furthermore, a 2015 report[37] suggested that downregulation of T-cell co-stimulation markers was associated with T-cell exhaustion and poor outcomes in inflammatory and autoimmune diseases. Although IPF is not generally considered an autoimmune disease, T-cell exhaustion is a mechanism that should be explored.

Additionally, other members of the 52-gene expression signature might also provide some clues about the role of immune aberrations in IPF. For example, MCEMP1 is one of the outcome predictive genes that encodes a transmembrane protein isolated from human mast cells[38] that are known to work in concert with fibroblasts to aggravate pulmonary fibrosis[39] or FLT3, a strong nintedanib-responsive tyrosine kinase with unknown roles in pulmonary fibrosis.

In summary, the 52-gene risk profiles have been found to be reproducible predictors of outcome in patients with IPF. The enhanced outcome prediction accuracy when 52-gene risk profiles are added to the G-GAP index and the association of changes in genomic risk profiles with changes in FVC, survival, and potential response to antifibrotic therapy indicate that the 52-gene signature can be used as a blood test for risk stratification and disease monitoring in patients with IPF.

Determination of Risk Profile: Scoring Algorithm of Molecular Subphenotypes (SAMS)

The present disclosure makes use of the Scoring Algorithm of Molecular Subphenotypes (SAMS) system. The algorithm was developed to identify novel molecular subphenotypes based on the expression of a predefined set of increased and decreased genes in a given sample. The up and down scores of SAMS are calculated using the product of two variables: the proportion of genes expected to be increased or decreased per patient and their normalized expression levels.

For the 52-gene profile, up and down scores are calculated based on seven increased genes (PLBD1, TPST1, MCEMP1, IL1R2, HP, FLT3, S100A12) and 45 decreased genes (LCK, CAMK2D, NUP43, SLAMF7, LRRC39, ICOS, CD47, LBH, SH2D1A, CNOT6L, METTL8, ETS1, C2orf27A, P2RY10, TRAT1, BTN3A1, LARP4, TC2N, GPR183, MORC4, STAT4, LPAR6, CPED1, DOCK10, ARHGAP5, HLA-DPA1, BIRC3, GPR174, CD28, UTRN, CD2, HLA-DPB1, ARL4C, BTN3A3, CXCR6, DYNC2LI1, BTN3A2, ITK, SNHG1, CD96, GBP4, S1PR1, NAP1L2, KLF12, IL7R). The genes and their expression patterns are provided in Table 7. The calculation is performed in four steps:

1) Gene normalization: The expression of each gene is normalized (subtracted) to the geometric mean of all the samples in each independent cohort. The geometric mean is specific to each gene and is calculated by taking the nth root of the product of n numbers. This step is performed in order to determine whether the expression of a gene is either increased or decreased in a patient when compared to other patients in the same cohort.

2) Calculation of the proportion of up and down-regulated genes: Given that the 52-gene signature is based on seven increased and 45 decreased genes, the proportion of genes expected to be either increased or decreased can be estimated per patient to calculate up and down scores. That is, if patient X has five increased genes out of the seven genes expected to be increased then the proportion of increased genes for this patient is 0.714 (5/7). If the same patient has five decreased genes out of the 45 genes expected to be decreased, then the proportion of decreased genes for the same patient is 0.111 (5/45).

3) Sum of the normalized expression values of increased and decreased genes: The sum of the normalized expression values (calculated in Step 1), is calculated per patient for the entire set of increased genes and for the entire set of decreased genes separately. For patient X in the example above, if the normalized expression values of the five increased genes are 0.213+0.273+0.295+0.485+0.923, then the sum of these expression values is 2.190. If the normalized expression values of the five decreased genes for the same patient are −0.202 (+) −0.140 (+) −0.086 (+) −0.082 (+) −0.066, then the sum of these expression values is −0.578.

4) Calculation of the product between the sum of normalized expression values and the proportion of increased or decreased genes: For this step, the sum of increased genes calculated in Step 3 is multiplied by the proportion of increased genes calculated in Step 2. For patient X in the example above the product between these two variables is 0.714*2.190=1.564; this value is the up score. The same process is followed for the down score calculation and the product between these two variables for patient X is 0.111*−0.578=−0.064; this value is the down score. If a patient does not have any of the seven genes expected to be increased, then the up score is 0. The same is true for patients without any of the 45 genes expected to be decreased.

To determine risk profiles, patients with up scores above the median value and down scores below the median value in each independent cohort are classified as high risk. Patients without this pattern of expression were classified as low risk. To identify significant differences between up and down-scores across cohorts an ANOVA test was used (FIGS. 6A-6B). Significance was defined as $p<0.05$. High risk individuals are more likely to have a poor disease outcome than low risk individuals—the former have a greater likelihood of poor disease outcome than the latter. Examples of poor disease outcome include death and need of lung transplant.

As described above, a determination of "high risk" may help guide a physician's treatment of the individual, such as ordering a transplant evaluation or determining whether or not the individual is responding to treatment. Alternatively, a determination of "low risk" may also help guide a physician's treatment of the individual, such as managing the individual's symptoms as opposed to seeking a transplant.

Time course analysis is also within the scope of the present disclosure. The up scores and down scores of an individual can be determined at two different times. The change in up score and down score can then be used to determine whether the individual fits the high risk profile. Patients are classified as high risk if their up scores increased by at least 10% (for example 15%, 20%, 30%, 40%, 50, 60%, 70%, 80%, 90%, 100%, and so on) at a later time point while their down scores decreased by at least 10% (for example 15%, 20%, 30%, 40%, 50, 60%, 70%, 80%, 90%, 100%, and so on). In contrast, patients that did not have up scores increase by 10% or greater (for example 15%, 20%, 30%, 40%, 50, 60%, 70%, 80%, 90%, 100%, and so on) and who did not have down scores decrease by 10% or greater (for example 15%, 20%, 30%, 40%, 50, 60%, 70%, 80%, 90%, 100%, and so on), are classified as low risk. Samples may be taken within one month of each other or years apart; for example 15 days, 20 days, 30 days, 1 month, 2 months, 3 months, 4 months, 5 months, 6 months, 8 months, 10 months, 12 months, 14 months, 16 months, 18 months, 20 months, 22 months, 2 years, 2.5 years, 3 years, 4 years, 5 years, 6 years, 7 years, 8 years, 9 years, 10 years, or even longer.

TABLE 7

52-gene signature. Gene description, symbol and direction

| Gene Name | Gene symbol | Cox score |
|---|---|---|
| Phospholipase B domain containing 1 | PLBD1 | Up |
| Tyrosylprotein sulfotransferase 1 | TPST1 | Up |
| Chromosome 19 open reading frame 59 (mast cell-expressed membrane | C19orf59 | Up |
| Interleukin 1 receptor, type II | IL1R2 | Up |
| Haptoglobin | HP | Up |
| FMS-related tyrosine kinase 3 | FLT3 | Up |
| S100 calcium binding protein A12 | S100A12 | Up |
| Lymphocyte-specific protein tyrosine kinase | LCK | Down |
| Calcium/calmodulin-dependent protein kinase II delta | CAMK2D | Down |
| Nucleoporin 43 kDa | NUP43 | Down |
| SLAM family member 7 | SLAMF7 | Down |
| Leucine rich repeat containing 39 | LRRC39 | Down |
| Inducible T cell co-stimulator | ICOS | Down |
| CD47 molecule | CD47 | Down |
| Limb bud and heart development | LBH | Down |
| SH2 domain containing 1A | SH2D1A | Down |
| CCR4-NOT transcription complex, subunit 6-like | CNOT6L | Down |
| Methyltransferase like 8 | METTL8 | Down |
| V-ets erythroblastosis virus E26 oncogene homolog 1 | ETS1 | Down |
| Chromosome 2 open reading frame 27A | C2orf27A | Down |
| Purinergic receptor P2Y, G-protein coupled, 10 | P2RY10 | Down |
| T cell receptor associated transmembrane adaptor 1 | TRAT1 | Down |
| Butyrophilin, subfamily 3, member A1 | BTN3A1 | Down |
| La ribonucleoprotein domain family, member 4 | LARP4 | Down |
| Tandem C2 domains, nuclear | TC2N | Down |
| G protein-coupled receptor 183 | GPR183 | Down |
| MORC family CW-type zinc finger 4 | MORC4 | Down |
| Signal transducer and activator of transcription 4 | STAT4 | Down |
| Lysophosphatidic Acid Receptor 6 | LPAR6 | Down |
| Chromosome 7 open reading frame 58 (Cadherin-like and PC-esterase | C7orf58 (CPED1) | Down |
| Dedicator of cytokinesis 10 | DOCK10 | Down |
| Rho GTPase activating protein 5 | ARHGAP5 | Down |
| Major histocompatibility complex, class II, DP alpha 1 | HLA-DPA1 | Down |
| Baculoviral IAP repeat containing 3 | BIRC3 | Down |
| G protein-coupled receptor 174 | GPR174 | Down |
| CD28 molecule | CD28 | Down |
| Utrophin | UTRN | Down |
| CD2 molecule | CD2 | Down |
| Major histocompatibility complex, class II, DP beta 1 | HLA-DPB1 | Down |
| ADP-ribosylation factor-like 4C | ARL4C | Down |
| Butyrophilin, subfamily 3, member A3 | BTN3A3 | Down |
| Chemokine (C—X—C motif) receptor 6 | CXCR6 | Down |
| Dynein cytoplasmic 2 light intermediate chain 1 | DYNC2LI1 | Down |
| Butyrophilin, subfamily 3, member A2 | BTN3A2 | Down |
| IL2 inducible T cell kinase | ITK | Down |
| Small nucleolar RNA host gene 1 | SNHG1 | Down |
| CD96 molecule | CD96 | Down |
| Guanylate binding protein 4 | GBP4 | Down |
| Sphingosine-1-phosphate receptor 1 | S1PR1 | Down |
| Nucleosome assembly protein 1-like 2 | NAP1L2 | Down |
| Kruppel-like factor 12 | KLF12 | Down |
| Interleukin 7 receptor | IL7R | Down |

Assessment of Sample

The present disclosure, in some aspects, provides a method of assessing a sample using the 52-gene risk signature. Samples may come from an individual, such as a human and may be blood, peripheral blood mononuclear cells (PBMCs), or RNA obtained from such cells. A sample may be collected using any method known in the art, for example, via a routine blood draw. RNA extraction is also known in the art; exemplary methods include gelatin extraction, silica, glass bead, or diatom extraction, guanidine-thiocyanate-phenol solution extraction, guanidine-thiocyanate acid-based extraction, centrifugation through a cesium chloride or similar gradient, and phenol-chloroform-based extraction. In a particular embodiment, the RNA extraction may be performed using an RNA kit, such as the PAXgene Blood RNA Kit. Other kits are commercially available.

RNA concentration and purity can be determined by those skilled in the art employing technologies well known to the skilled artisan such spectrophotometry, gel analysis, and other like technologies. In one example, RNA concentration and purity may be evaluated using a NanoDrop spectrophotometer. RNA integrity can be further measured using methods known in the art, including with the use of a TapeStation (Agilent).

Expression levels of different genes may be determined using methods known in the art. Examples include Northern blots, Western blots, microarray analysis, reverse transcription polymerase chain reaction (RT-PCR). For example, the Nanostring preparation station and digital analyzer may be used.

The sample may be analyzed using the SAMS method described above. Additionally, the GAP index for idiopathic pulmonary fibrosis mortality may be used in conjunction with the 52-gene profile. The GAP index provides 1-, 2-, and 3-year mortality estimates for IPF patients based on gender, age, predicted forced vital capacity (FVC) and predicted diffusing capacity of the lung for carbon monoxide (DLCO).

Kits

The present disclosure also provides kits for use in predicting patient outcome, for example, in idiopathic pulmonary fibrosis. Such kits can include the means for collecting one or more blood samples, RNA extraction, and measuring gene expression of the 52 genes. For example, the kit may include a set of probes comprising one or more probes or primers for each of the following genes: PLBD1, TPST1, C19orf59 (MCEMP1), IL1R2, HP, FLT3, S100A12, LCK, CAMK2D, NUP43, SLAMF7, LRRC39, ICOS, CD47, LBH, SH2D1A, CNOT6L, METTL8, ETS1, C2orf27A, P2RY10, TRAT1, BTN3A1, LARP4, TC2N, GPR183, MORC4, STAT4, LPAR6, C7orf58 (CPED1), DOCK10, ARHGAP5, HLA-DPA1, BIRC3, GPR174, CD28, UTRN, CD2, HLA-DPB1, ARL4C, BTN3A3, CXCR6, DYNC2LI1, BTN3A2, ITK, SNHG1, CD96, GBP4, S1PR1, NAP1L2, KLF12, and IL7R.

In some embodiments, the kit can comprise instructions for use in accordance with any of the methods described herein. The included instructions can comprise a description of gene expression measurement and interpretation of results. The kit may further comprise a description of selecting an individual suitable for treatment based on identifying whether that individual has the target disease, e.g., IPF.

Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for predicting IPF outcome. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like.

Kits may optionally provide additional components such as buffers and interpretive information. Normally, the kit comprises a container and a label or package insert(s) on or associated with the container. In some embodiments, the invention provides articles of manufacture comprising contents of the kits described above.

Exemplification

Figure 2A:
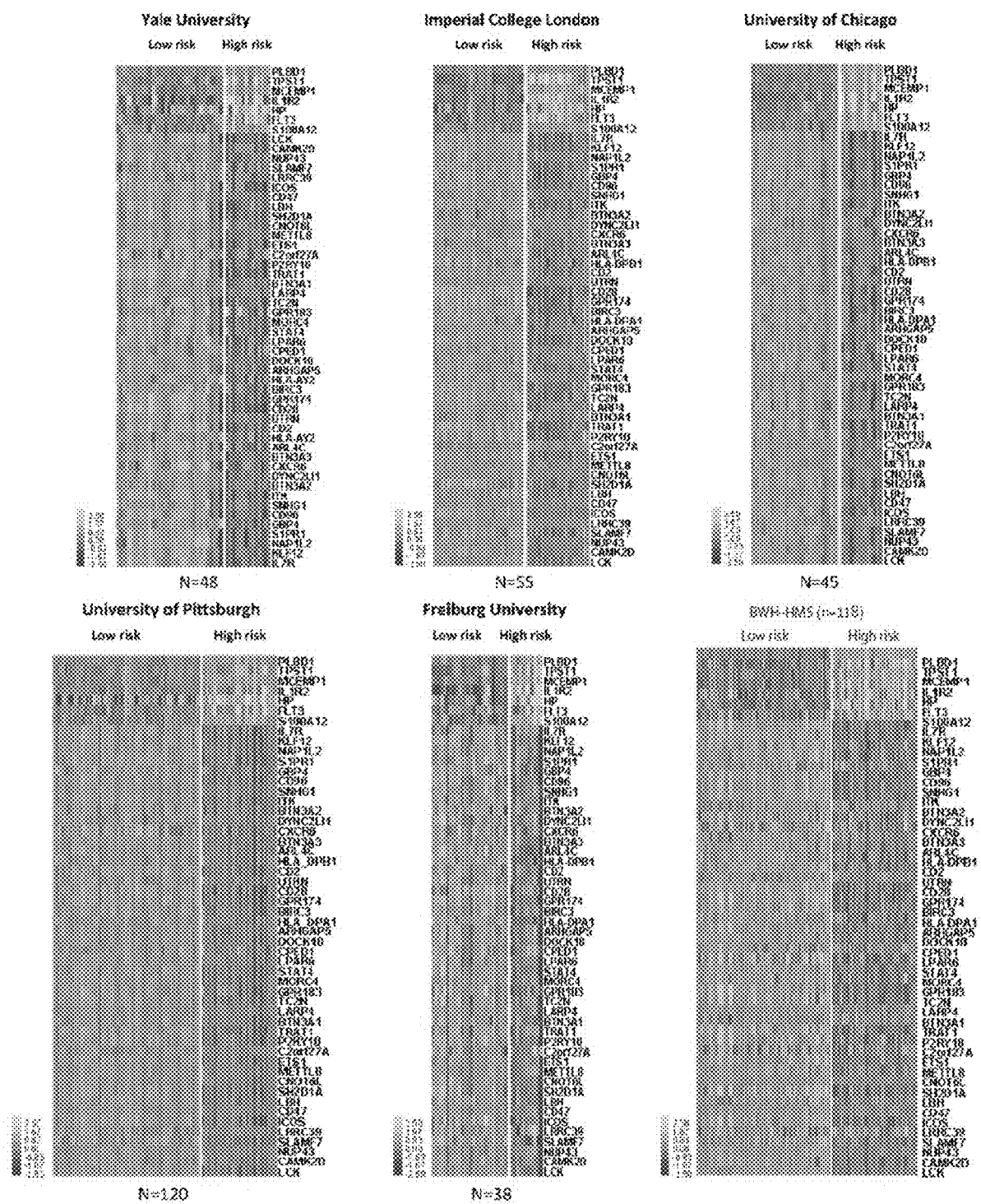
FIGS. 2A-2B. Genomic risk profiles based on the 52-gene signature are predictive of outcome in IPF.
Figure 2B:
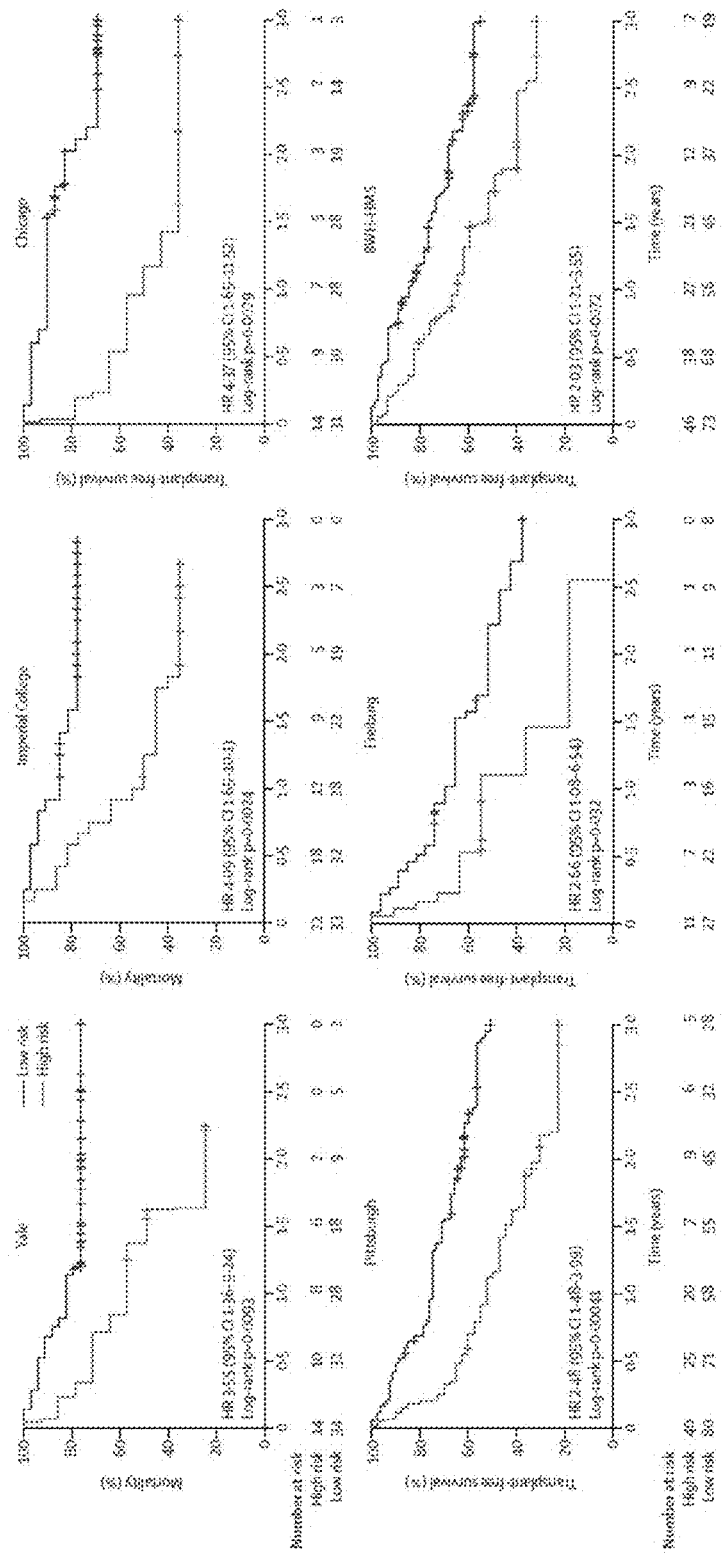

Participants with idiopathic pulmonary fibrosis (IPF) were recruited for the six cohorts (Yale University, New Haven, Conn., USA, n=48; Imperial College London, London, UK, n=55; University of Chicago, Chicago, Ill., USA, n=45; University of Pittsburgh, Pittsburgh, Pa., USA, n=120; University of Freiburg, Freiburg Breisgau, Germany, n=38; and Brigham and Women's Hospital-Harvard Medical School [BWH-HMS], Boston, Mass., USA n=119) between July 2004 and August 2015 (Table 1). Patients were classified into high-risk and low-risk groups using the Scoring Algorithm of Molecular Subphenotypes (SAMS). Up scores and down scores did not differ significantly between cohorts, suggesting a similar distribution of patients with 52-gene, high-risk profiles in each cohort (FIG. 5). SAMS scores separated patients into high-risk and low-risk groups with similarity in gene expression patterns within risk groups across the various cohorts (FIG. 2A). Univariate Cox proportional hazards models showed that patients in the high-risk group had significantly ($p<0.050$) higher mortality (Yale and Imperial College cohorts) or lower transplant-free survival (Chicago, Pittsburgh, Freiburg, and BWH-HMS cohorts) when compared with patients in the low-risk group (FIG. 2B). The hazard ratios (HR) for mortality and transplant-free survival ranged from 2.03 to 4.37, which indicate an increased risk of dying or having a lung transplant during follow-up in each independent cohort by at least double for patients with a 52-gene, high-risk profile.

To determine how outcome prediction using 52-gene risk profiles compared with serum MMP7, MMP7 concentrations were measured using ELISA in Pittsburgh cohort patients with simultaneous PBMC and serum collections (n=114) and their transplant-free survival prediction performance was compared with the C-index. The analysis showed that the C-index for transplant-free survival prediction in the Pittsburgh cohort was significantly higher ($p=0.011$) when using 52-gene, genomic risk profiles (C-index 0.72, 95% CI 0.659-0.779) versus MMP7 concentrations in serum (0.61, 0.535-0.683).

Figure 3A:
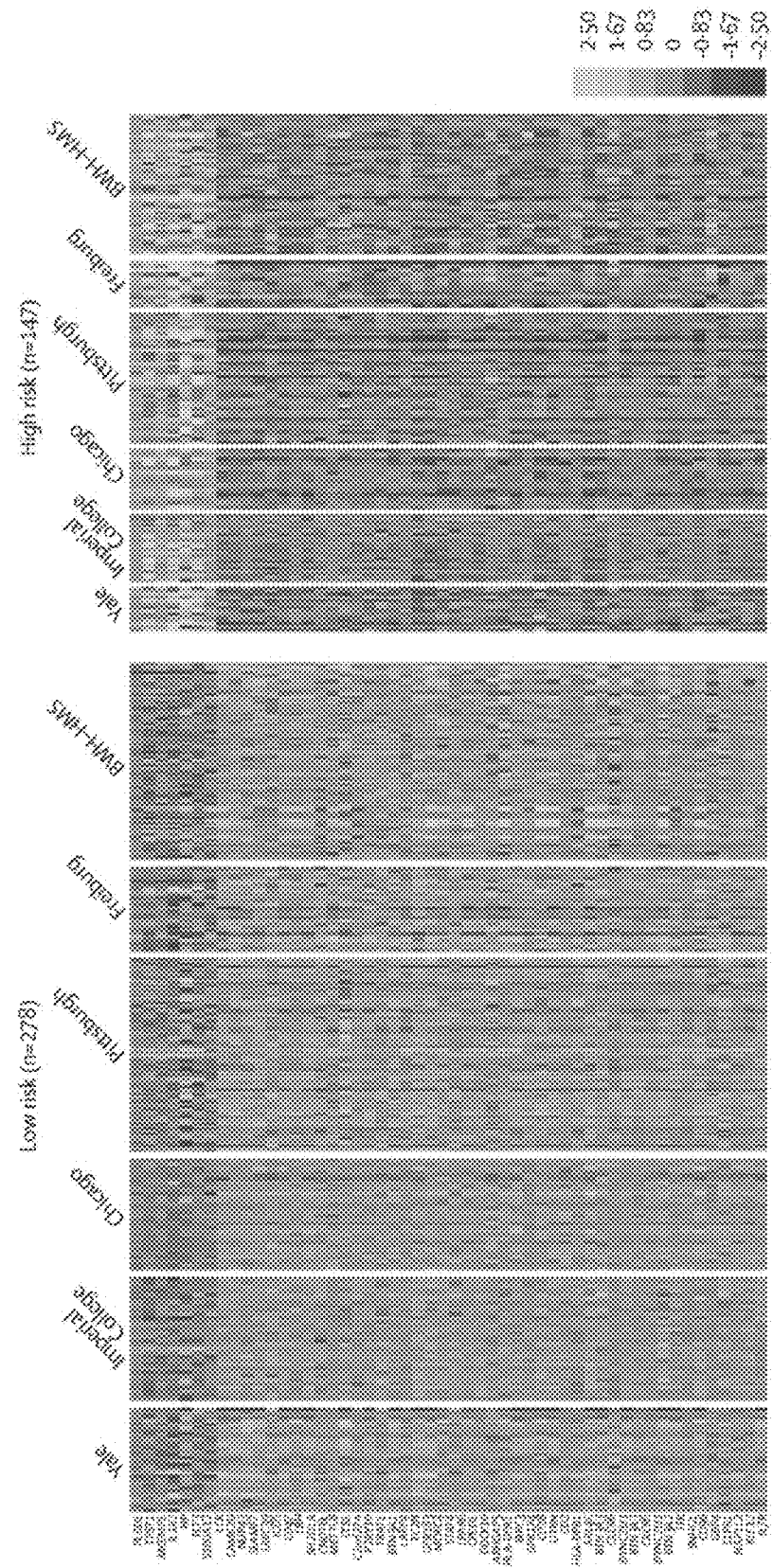
FIGS. 3A-3E. 52-gene risk profiles and outcomes independent of demographic and clinical variables.
Figure 3B:
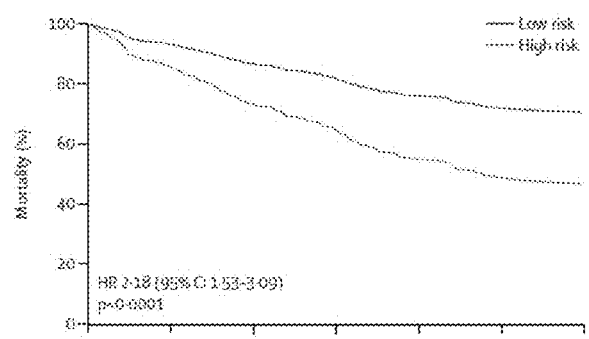
Figure 3C:
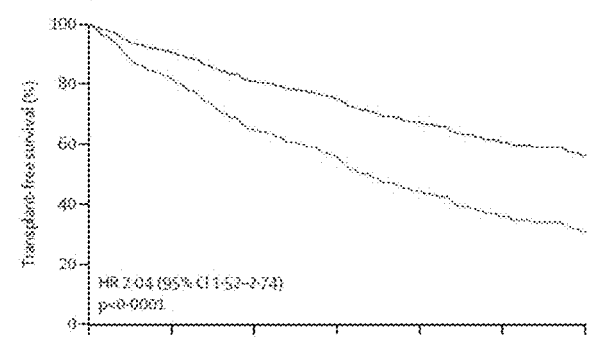
Figure 3D:
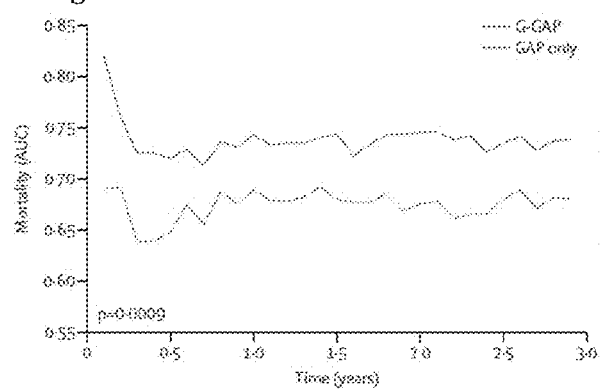
Figure 3E:
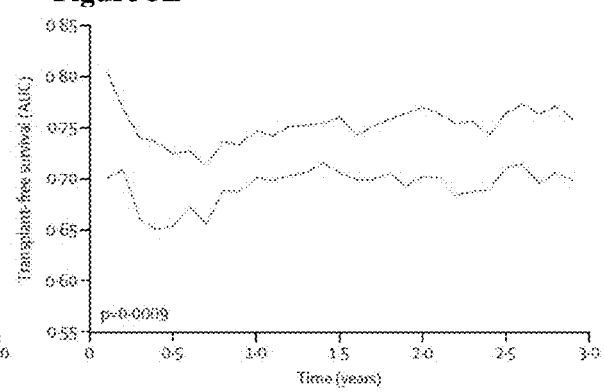

To identify demographic and clinical characteristic differences between 52-gene risk profiles, a pooled data analysis was performed using data from all 425 patients with IPF (FIG. 3A). High-risk patients were predominantly white men with lower FVC % and DLCO % at presentation. High-risk patients used immunosuppressants more than low-risk patients (Table 2). A high-risk, 52-gene profile was independently predictive of mortality (HR 2.18, 95% CI 1.53-3.09; $p<0.0001$) or transplant-free survival (2.04, 1.52-2.74; $p<0.0001$; FIGS. 3B, 3C) after adjusting for age, sex, FVC %, and immunosuppressive therapy in the pooled dataset. To account for possible cohort heterogeneity, multivariate competing risk and Cox proportional hazards models stratified by cohort were analyzed using the pooled data. The results did not differ significantly (2.36, 1.67-3.35; $p<0.0001$ for mortality; and 2.08, 1.54-2.80; $p<0.0001$ for transplant-free survival). Because of the known adverse effects of immunosuppressive therapy on the survival of patients with IPF,[20] the analysis was repeated using only patients who did not receive immunosuppression. The 52-gene, high-risk genomic profile was also independently predictive of mortality (2.27, 1.54-3.35, $p<0.0001$) or transplant-free survival (2.13, 1.54-2.96; $p<0.0001$) in this dataset after excluding patients on immunosuppressants (FIGS. 6A-6B). A prediction model based on the calculated G-GAP index outperformed all other prediction models studied (Tables 3 and 4) and significantly improved accuracy prediction of mortality or transplant-free survival (FIGS. 3D, 3E). The maximal AUC changed by 13.0% (69.0-82.0%) for a 30-day mortality prediction and 10.6% (70.0-80.6%) for a transplant-free survival prediction.

To determine the association between changes in up scores and down scores over time with FVC, a linear mixed effect model adjusted for age and sex was used in the Pittsburgh and Yale cohorts. In both cohorts, up scores were negatively associated with FVC and down scores were positively associated with FVC. The association of up scores with FVC was −0.025 (95% CI −0.039 to −0.011; $p=0.00036$) in the Pittsburgh cohort and −0.010 (−0.017 to −0.004; $p=0.0043$) in the Yale cohort. Similarly, the association of down scores with FVC was 0.008 (0.005 to 0.011; $p<0.0001$) in the Pittsburgh cohort and 0.027 (0.004 to 0.051; $p=0.029$) in the Yale cohort.

Figure 4A:
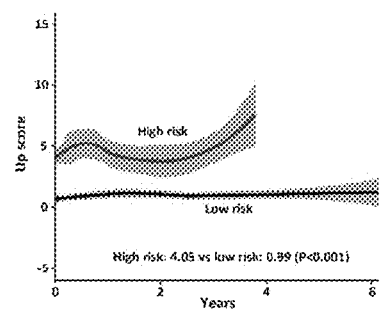
FIGS. 4A-4E. 52-gene signature trends over time demonstrate association with disease progression and survival. Up (FIG. 4A) and down (FIG. 4B) scores from SAMS, and FVC volumes (FIG. 4C) do not shift over time in high-risk versus low-risk groups (Pittsburgh cohort).
Figure 4B:
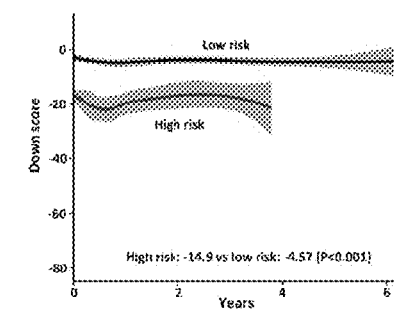
Figure 4C:
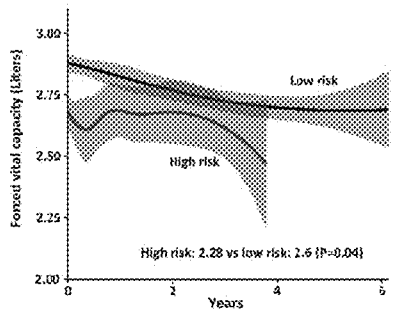

To determine whether high-risk or low-risk patients who were not on antifibrotic drugs (Pittsburgh cohort) shifted their risk profile, up scores, down scores, and FVC were plotted and compared over time in high-risk versus low-risk groups using a linear mixed effect model. The results indicate no shift in risk profiles or FVC (FIGS. 4A-4C), as confirmed by the linear mixed effect model. This model showed a significant difference for up scores (4.05 for high risk vs 0.99 for low risk; p<0.0001), down scores (−14.9 for high risk vs −4.57 for low risk; p<0.0001), and FVC (2.28 L for high risk vs 2.60 L for low risk; p=0.046) across time in this cohort.

Figure 4D:
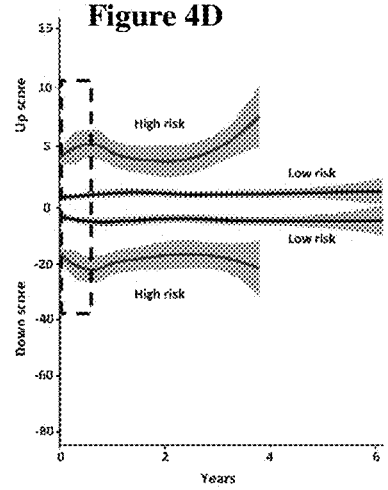
Figure 4E:
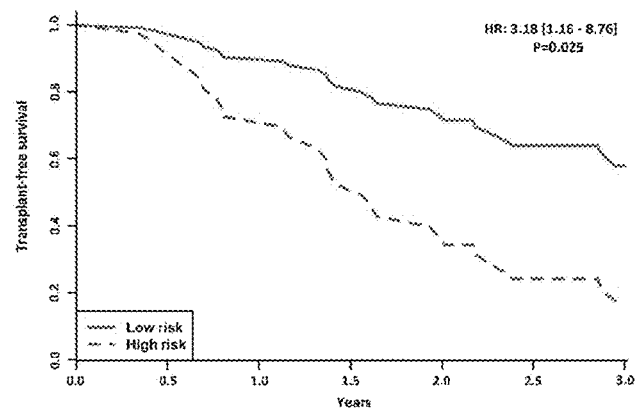

Whether substantial changes in SAMS scores over time were predictive of IPF survival in patients not on antifibrotic drugs was also examined (Pittsburgh cohort). Since relative changes in FVC of 10% or higher have been associated with decreased IPF survival,[21,22] it was thought that a relative increase in up score and a simultaneous decline in down score of 10% or lower was also predictive of IPF survival. Univariate and multivariate Cox models (Table 5) showed that a simultaneous 10% or higher increase in up score and decrease in down score (bidirectional changes) between two measurements obtained 30 days apart (FIG. 4D) was significantly predictive of decreased transplant-free survival (HR 3.18, 95% CI 1.16-8.76; p=0.025; FIG. 4E).

To determine the effect of antifibrotic drugs on 52-gene risk profiles, up scores and down scores over time in the Yale time course cohort were plotted. Low-risk profile patients exhibited the same patterns observed in the Pittsburgh cohort, but high-risk profile patients exhibited shifts in up scores and down scores (FIGS. 9A-9B). Because a higher proportion of high-risk patients were initiated on antifibrotic therapy (90%) than low-risk patients (59%; Table 6), the interaction between changes in scores and response to therapy was analyzed. In patients who exhibited a simultaneous decrease in up score and increase in down score, an average increase in FVC (0.06 L/year) was observed, while in patients that did not exhibit these changes in scores, an average decrease in FVC (−0.21 L/year; p=0.005; FIG. 9C) was observed.

Methods

Patients and Cohorts

Figure 1A:
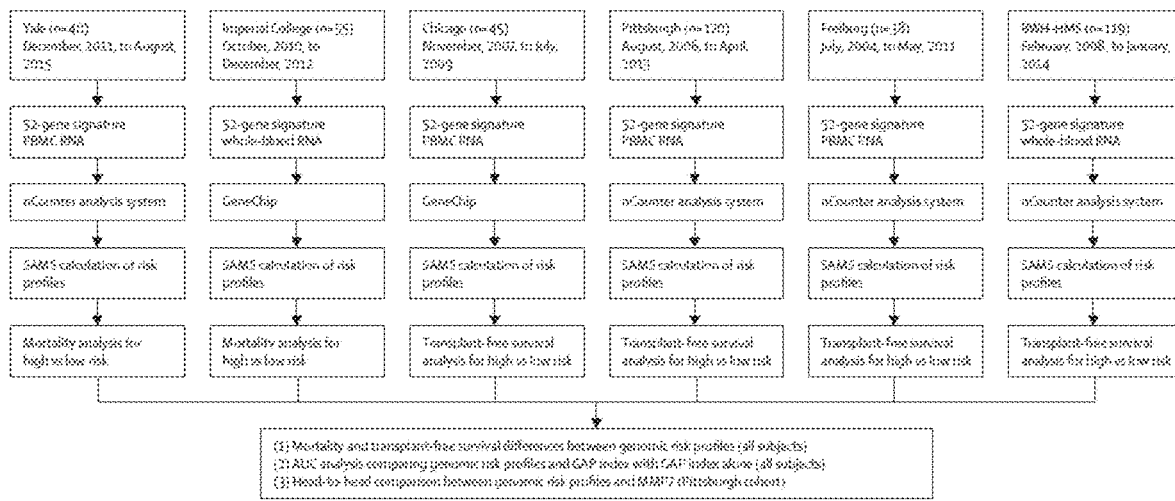
FIGS. 1A-1B. Study design. The outline summarizes the time to event (FIG. 1A) and time course analysis (FIG. 1B) design for this study including the cohorts, blood compartments, experiments and statistical methods used in each independent cohort and in the pooled data analysis. Time is presented in years (average and range, in parentheses).
Figure 1B:
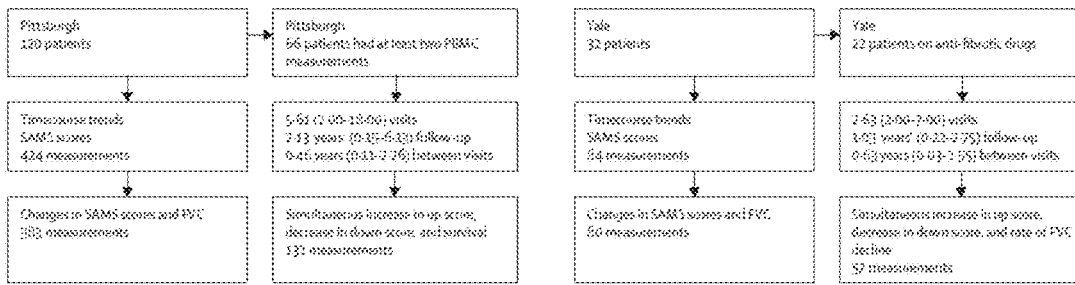

Patients were recruited from the Universities of Yale (n=48), Imperial College London (n=55), Chicago (n=45), Pittsburgh (n=120), Freiburg (n=38) and Harvard (n=119). For time course analyses, samples were available from Pittsburgh and Yale cohort participants (FIG. 1B). IPF diagnosis was established by a multidisciplinary group at each institution following ATS/ERS guidelines[10]. The studies were approved by the institutional review boards at each institution, and informed consent was obtained from all patients. Demographic, clinical information, spirometric data and diffusion of the lung for carbon monoxide (DLCO) were collected at the time of blood draw. The Gender, Age, and Physiology (GAP) index was calculated as reported by Ley and colleagues[3].

Sample Collection, RNA Extraction, and Quality Assessment

PBMC collection, total RNA extraction, and quality assessment methods were done in the Yale, Chicago, Pittsburgh, and Freiburg cohorts as previously described.[6] For the BWH-HMS and Imperial College cohorts, whole blood was collected using PAXgene blood RNA tubes (PreAnalytiX, Hombrechtikon, Switzerland) and total RNA was extracted with the PAXgene Blood RNA Kit (PreAnalytiX), following the manufacturer's protocol.

RNA concentration and purity (A260/A280) were measured using a NanoDrop spectrophotometer (NanoDrop Technologies). RNA quality and RNA integrity (RIN) was assessed using a TapeStation (Agilent).

52-Gene Signature Measurement

To validate the 52-gene signature in the Yale, Pittsburgh, Freiburg, and BWH-HMS cohorts, the nCounter analysis system was used (NanoString Technologies, Seattle, Wash., USA).[11] For the Imperial College cohort, the 52-gene signature was analyzed from a previously published gene expression dataset[12] of whole blood (GEO accession number GSE93606). For the Chicago cohort, the expression of the 52-gene signature was analyzed from a previously published gene expression dataset[6] of PBMC from patients with IPF (GEO accession number GSE27957).

Briefly, 200 ng (Pittsburgh) and 100 ng (Yale, Freiburg and BWH-HMS) of total RNA per sample was hybridized with a custom code set generated based on the 52-gene signature (PLBD1, TPST1, MCEMP1, IL1R2, HP, FLT3, S100A12, LCK, CAMK2D, NUP43, SLAMF7, LRRC39, ICOS, CD47, LBH, SH2D1A, CNOT6L, METTL8, ETS1, C2orf27A, P2RY10, TRAT1, BTN3A1, LARP4, TC2N, GPR183, MORC4, STAT4, LPAR6, CPED1, DOCK10, ARHGAP5, HLA-DPA1, BIRC3, GPR174, CD28, UTRN, CD2, HLA-DPB1, ARL4C, BTN3A3, CXCR6, DYNC2LI1, BTN3A2, ITK, SNHG1, CD96, GBP4, S1PR1, NAP1L2, KLF12, IL7R) and the endogenous controls ACTB, GAPDH and GUSB for Yale, Pittsburgh and Freiburg cohorts and ACTB, B2M, CLTC, GAPDH, GUSB, HPRT1, POLRB1, RLP19 and TBP for BWH-HMS cohort. After hybridization, gene transcript counts were obtained using the Nanostring preparation station and digital analyzer. Gene expression values of the genes in the signature were normalized by cohort to an average of positive, spiked-in and endogenous controls as recommended by the manufacturer using the nSolver analysis software.

Gene expression microarrays were done in accordance with the Minimum Information About a Microarray Experiment guidelines. Gene normalization was done by cohort and $\log_2$-transformed gene expression values were used for statistical analyses.

MMP7 Measurement

To measure MMP7, serum samples were obtained from Pittsburgh cohort patients who had PBMC collected simultaneously in the time-to-event analysis. The MMP7 ELISA assay has been validated previously (R&D Systems, Minneapolis, Minn., USA).[13,14]

Scoring Algorithm of Molecular Subphenotypes (SAMS)

The Scoring Algorithm of Molecular Subphenotypes (SAMS) is a classification algorithm of gene expression data generated from the calculation of two scores (up and down scores). To determine 52-gene risk profile in each independent cohort, patients with up scores above the median value and down scores below the median value in each cohort were classified as high risk. Patients without this pattern of expression were classified as low risk. ANOVA was used to identify significant differences in SAMS scores between cohorts; the SAMS calculator is publicly available (gem.med.yale/edu/SAMASWeb3/index.jsp).

The up and down-scores are calculated using the product of two variables: the proportion of genes expected to be increased or decreased per patient and their normalized expression levels. The following steps summarize the calculation of SAMS scores: Step 1: the expression of each gene of the 52-gene signature is normalized to the geometric mean of all the samples in the cohort. The $\log_2$ value of the gene is subtracted from the geometric mean of the same gene in all the samples in the cohort. A gene with a positive value is considered increased, and a gene with a negative value is considered decreased. Step 2: to determine increased and decreased ratios, the ratio is calculated by dividing the number of genes changed in a certain direction (increased or decreased) in a sample by the number of genes expected to change in the same direction. The 52-gene signature contains seven increased and 45 decreased genes. Thus, the increased ratio is calculated by dividing the number of actually increased genes by 7, and the decreased ratio is the number of actually decreased genes divided by 45. Step 3: sums of the values of increased or decreased genes are calculated per sample. Step 4: for the calculation of the scores, the up score is derived by multiplying the sum of the values of the increased genes (calculated in step 3) by the increased ratio (calculated in step 2) and the down score by multiplying the sum of the decreased genes by the decreased ratio. Because the gene expression values are $\log_2$, the up score will be positive and the down score will be negative.

Time to Event Analysis

Patients were followed from blood draw until death, loss of follow up, or transplant. Because two cohorts (Yale and Imperial college) did not contain transplants, different outcome definitions: transplant-free survival (TFS) in Chicago, Pittsburgh, Freiburg and Harvard and mortality in Yale and Imperial College. TFS was the primary outcome for univariate analysis in Chicago, Pittsburgh, Freiburg and BWM-HMS cohorts given that selected patients in each one of these four cohorts underwent lung transplantation during follow up. The association between genomic risk profiles and outcomes was determined by univariate Cox Proportional-Hazard models. For TFS, both transplants and deaths were considered events. To determine whether genomic risk profiles were outcome predictive after adjusting for age, gender, forced vital capacity (FVC) volume and immunosuppressive therapy, data from all cohorts was pooled and adjusted for age, sex, percentage of predicted forced vital capacity (FVC), and immunosuppressive therapy. Multivariate competing risk[15] and Cox proportional-hazard[16] models were applied to the pooled data to determine association with mortality or TFS respectively. For mortality analyses in the pooled data, transplants were considered a competing risk (FIG. 1A). For survival analyses the survival, cmprsk, and timeROC packages of the R environment. Differences in mortality and TFS between patients with high and low risk genomic profiles were evaluated using cumulative incidence and Kaplan Meier curves, respectively.

To test whether genomic risk profile information could improve outcome prediction when used in combination with the GAP index[3], competing risk[15] and Cox proportional-hazard[16] models were fit as follows: GAP only, genomic only (high and low), GAP index with genomic risk profiles, and GAP and genomic (G-GAP) index. The G-GAP index was calculated by adding three points (the maximum score in the GAP index) to the GAP index if a patient had a high risk genomic profile and no points if he/she had a low risk profile. To compare the predictive performance of these models, time-dependent receiver operating characteristic (ROC) for censored data[17] and area under the curve (AUC) using a 10-fold cross-validation procedure were employed. To compare the predictive performance of two prediction models, the difference in the area under the two AUC curves was calculated. This difference provided the overall predictive performance across all possible time points for the two models. To account for the high correlations of AUC values at different time points, a permutation test, based on 1000 permutations, was used to calculate the P value for the differences in AUC.

MMP7 and 52-gene risk profiles were compared head-to-head using the Concordance index (C-index), an equivalent of the AUC in an ROC, a well-accepted measure of the probability that predicting the outcome is better than chance.[18] GAP index was excluded from the comparisons between 52-gene risk profiles and MMP7.

Time Course Analysis

Time course analyses were performed in Pittsburgh and Yale cohort patients (FIGS. 1B and 8A-8B). Trends in SAMS scores and FVC were plotted to identify shifts in genomic risk profiles over time. In order to visualize time course trends of increased and decreased genes in the Pittsburgh (N=424 measurements) (FIG. 8A) and Yale cohort (N=84 measurements), the expression of each gene was normalized to the geometric mean of all 424 samples in case of the Pittsburgh cohort and to all of the 84 samples in case of the Yale cohort. Up and down scores of SAMS were calculated for each patient at each time point, in each cohort independently. In order to plot up and down score trends across time and to minimize the effect of different follow-up times for different subjects, the scores in each subject belonging to either high or low 52-gene risk profile were centered, across all time points. The centered values were normalized to the baseline up or down score for patients in the high or low risk groups, respectively. The FVC trends for patients belonging to high and low risk genomic groups in the Pittsburgh cohort were calculated using the same procedure described above for Pittsburgh cohort patients. The total number of Pittsburgh cohort patients with FVC measurements (N=383) are summarized in FIG. 8B. Point wise confidence intervals were calculated for each variable in each time point. To identify statistically significant differences in up and down scores and FVC across time in Pittsburgh cohort patients belonging to high vs low risk groups, the average differences over time were calculated for each variable and in each risk group by using a linear mixed-effect (LME) model[19] with random intercepts. Results were adjusted to age, gender, FVC and immunosuppression use.

A linear mixed-effect model was also used to study the associations between relative changes in up and down scores and relative changes in FVC in patients with simultaneous measurements. To determine the association between bidirectional changes in SAMS scores and survival, the relative changes in up and down scores for each IPF patient were calculated based on their first two visits, adjusting to the length of time interval. Linear mixed effect models were adjusted by patient's age, sex, and therapy (immunosuppression therapy in the Pittsburgh cohort and antifibrotic therapy in the Yale cohort). Antifibrotic therapy was initiated after the baseline sample was collected and defined as the use of pirfenidone or nintedanib.

To determine the association between changes in SAMS scores and survival, the relative changes in up score and down score for each patient with IPF were calculated on the basis of their first two visits, with adjustment to the duration of time intervals. This analysis was performed using the first two visits given that 66 of patients had at least two subsequent measurements. For example, if patient X has an up score s1 at t=0, and an up score s2 at t=4 months, then the relative changes in up score in six months for this patient is calculated as follows: 6*(s2−s1)/s1/4. Thus, for each of the 66 patients with at least two subsequent visits, the relative changes at each month going from one to six months for both up and down scores were calculated. Patients were classified as high risk if relative changes in up and down scores between two subsequent visits occurred simultaneously and were ≥10%. A CoxPH model was used to determine the association between bidirectional changes in SAMS scores and TFS after adjusting for age, gender, FVC and immunosuppression use (Table 5).

Finally, a linear mixed effect model was used to compare the rate of FVC decline per year in patients with IPF from the Yale cohort who had a simultaneous decrease in down score and increase in up score (n=6) from those patients with other time course changes in SAMS scores (n=16), after initiation of antifibrotic therapy. Statistical significance was defined as two-sided p values less than 0.05. Analyses were done using R version 3.4.0.

Survival Analysis Based on the 52-Gene Signature in Control Individuals

To determine whether the 52-gene signature discriminated risk profiles associated with increased mortality in old subjects without IPF, PBMC gene expression was studied in a cohort of nonagenarian individuals born in 1920 who participated in the Vitality 90+ Study.[40] PBMC were collected from these individuals when they were 90 years old and gene expression microarrays were performed.[41] Subjects were followed from blood draw until death or survival. Follow up time was limited to three years to be consistent with the study. The full dataset is available in GEO under GSE65218. Genomic risk profiles based on the 52-gene signature in PBMC were calculated using SAMS and the association between risk profiles and all-cause mortality was evaluated using Kaplan Meier curves in this cohort (FIGS. 9A-9C).

Tables

TABLE 2

Clinicopathological characteristics of the IPF patient in the two risk groups (pooled data). P-values were calculated using the Fisher's exact test except for age, pulmonary function tests and GAP index where an unpaired, two tailed, t-test was used. FVC %, forced vital capacity, percent predicted, DLCO %, carbon monoxide diffusing capacity, percent predicted. FEV1 %, forced expiratory volume in 1 second, percent predicted. HRCT, high-resolution computed tomography. UIP, usual interstitial pneumonia.

| Characteristic | Low risk (n = 278) | High risk (n = 147) | P-value[†] |
|---|---|---|---|
| Age (yr) | | | |
| Mean ± SD | 67.4 ± 7.9 | 68.4 ± 8.7 | 0.24 |
| Gender, n (%) | | | |
| Males | 198 (71.2) | 120 (81.6) | 0.019 |
| Females | 80 (28.8) | 27 (18.4) | |
| Race, n (%) | | | 0.077 |
| Caucasian | 257 (92.4) | 143 (97.7) | |
| Black | 10 (3.6) | 0 (0) | |
| Hispanic | 5 (1.8) | 3 (2) | |
| Other | 6 (2.2) | 1 (0.7) | |
| Smoking status, n (%) | | | 0.27 |
| Ever smoker | 185 (66.5) | 106 (72.1) | |
| Never smoker | 93 (33.5) | 41 (27.9) | |

TABLE 1

Clinicopathological characteristics of the IPF patients in the six cohorts for the time-to-event analysis.

| Characteristic | Yale (n = 48) | Imperial College (n = 55) | Chicago (n = 45) | Pittsburgh (n = 120) | Freiburg (n = 38) | BWH-HMS (n = 119) |
|---|---|---|---|---|---|---|
| Age at enrollment Mean ± SD | 70.8 ± 6.6 | 67.3 ± 8.1 | 67 ± 8.1 | 68.2 ± 8.5 | 66.8 ± 8.8 | 67 ± 8 |
| Sex | | | | | | |
| Male | 39 (81.3) | 36 (65.5) | 40 (88.9) | 87 (72.5) | 34 (89.5) | 82 (68.9) |
| Female | 9 (18.7) | 19 (34.5) | 5 (11.1) | 33 (27.5) | 4 (10.5) | 37 (31.1) |
| Race | | | | | | |
| Caucasian | 47 (97.9) | 52 (94.5) | 37 (82.3) | 118 (98.34) | 38 (100) | 108 (90) |
| Black | 0 (0) | 0 | 3 (6.6) | 1 (0.83) | 0 (0) | 6 (5) |
| Hispanic | 1 (2.1) | 0 | 5 (11.1) | 0 (0) | 0 (0) | 2 (1.5) |
| Other | 0 (0) | 3 (5.5) | 0 (0) | 1 (0.83) | 0 (0) | 3 (2.5) |
| Smoking status | | | | | | |
| Ever smoker | 37 (77.1) | 39 (70.9) | 27 (60) | 80 (66.7) | 27 (71.1) | 82 (68.9) |
| Never smokers | 11 (22.9) | 16 (29.1) | 18 (40) | 40 (33.3) | 11 (28.9) | 37 (31.1) |
| Immunosuppression use | | | | | | |
| No | 45 (93.8) | 46 (83.6) | 106 (88.3) | 90 (75.6) | 25 (65.8) | 43 (95.6) |
| Yes | 3 (6.2) | 9 (16.4) | 14 (11.7) | 29 (24.4) | 13 (34.2) | 2 (4.4) |
| Spirometry | | | | | | |
| FVC (%) | 73.6 ± 15.1 | 72.8 ± 20.4 | 61 ± 14.7 | 66.4 ± 18.6 | 65 ± 18 | 65.3 ± 18.5 |
| DLCO (%) | 39.6 ± 12.5 | 39.5 ± 14 | 43.3 ± 17.7 | 50.1 ± 18.9 | 46.8 ± 17.7 | 42.2 ± 16.2 |
| FEV1 (%) | 80.7 ± 19.2 | 73.5 ± 19 | 73.9 ± 17.3 | 78.3 ± 21.2 | 64.6 ± 16.2 | 70.8 ± 18.4 |
| GAP Index | | | | | | |
| Mean ± SD | 4.3 ± 1.4 | 3.9 ± 1.6 | 4.3 ± 1.6 | 3.8 ± 1.5 | 4.4 ± 1.5 | 3.9 ± 1.3 |
| Diagnosis, n (%) | | | | | | |
| HRCT + UIP Biopsy | 16 (33.3) | 0 | 64 (53.3) | 66 (55.5) | 16 (42.1) | 24 (53.3) |
| HRCT | 32 (66.7) | 55 (100) | 56 (46.7) | 53 (44.5) | 22 (57.9) | 21 (46.7) |

FVC %: Forced vital capacity percent predicted,
DLCO %: Carbon monoxide diffusing capacity percent predicted.
FEV1% Forced expiratory volume in 1 second percent predicted.
HRCT, high resolution computed tomography.
UIP: Usual Interstitial Pneumonia

TABLE 2-continued

Clinicopathological characteristics of the IPF patient in the two risk groups (pooled data). P-values were calculated using the Fisher's exact test except for age, pulmonary function tests and GAP index where an unpaired, two tailed, t-test was used. FVC %, forced vital capacity, percent predicted, DLCO %, carbon monoxide diffusing capacity, percent predicted. FEV1 %, forced expiratory volume in 1 second, percent predicted. HRCT, high-resolution computed tomography. UIP, usual interstitial pneumonia.

| Characteristic | Low risk (n = 278) | High risk (n = 147) | P-value[†] |
|---|---|---|---|
| Immunosuppression use, n (%) | | | |
| No | 252 (90.6) | 103 (70.1) | <0.001 |
| Yes | 26 (9.4) | 44 (29.9) | |
| Spirometry (mean ± SD) | | | |
| FVC % | 69.3 ± 18.4 | 62.7 ± 17.3 | <0.001 |
| DLCO % | 46 ± 17.3 | 40.9 ± 16.2 | 0.005 |
| FEV1 % | 76 ± 19.8 | 70.6 ± 18.4 | 0.007 |
| GAP Index | | | 0.002 |
| Mean ± SD | 3.9 ± 1.4 | 4.3 ± 1.5 | |
| Diagnosis, n (%) | | | 0.41 |
| HRCT + UIP biopsy | 126 (45.3) | 60 (40.8) | |
| HRCT | 152 (54.7) | 87 (59.2) | |

TABLE 3

Areas under the curve (AUC) and confidence intervals for mortality. The competing risk models evaluated for mortality are summarized as follows: GAP index (GAP score), Genomic (high vs low risk profile), GAP index + Genomic (GAP score + high vs low risk profile), G-GAP index (GAP score + three additional points for high risk profile)

| Years | GAP Index only | Genomic only | GAP + genomic | G-GAP index |
|---|---|---|---|---|
| 0.1 | 0.69 (95% 49.55, 88.44) | 0.788 (95% 67.68, 89.96) | 0.803 (95% 68.24, 92.37) | 0.82 (95% 71.28, 92.64) |
| 0.2 | 0.692 (95% 55.3, 83.03) | 0.652 (95% 51.39, 79.06) | 0.74 (95% 62.35, 85.71) | 0.761 (95% 65.47, 86.68) |
| 0.3 | 0.638 (95% 53.09, 74.55) | 0.64 (95% 53.24, 74.71) | 0.707 (95% 61.34, 80.15) | 0.725 (95% 63.6, 81.5) |
| 0.4 | 0.639 (95% 53.82, 74.01) | 0.646 (95% 54.76, 74.39) | 0.708 (95% 61.82, 79.87) | 0.725 (95% 63.88, 81.13) |
| 0.5 | 0.648 (95% 55.44, 74.14) | 0.629 (95% 53.51, 72.3) | 0.708 (95% 62.45, 79.17) | 0.72 (95% 63.85, 80.13) |
| 0.6 | 0.675 (95% 59.16, 75.8) | 0.633 (95% 54.82, 71.72) | 0.721 (95% 64.76, 79.37) | 0.729 (95% 65.72, 79.98) |
| 0.7 | 0.655 (95% 57.55, 73.45) | 0.62 (95% 53.74, 70.3) | 0.704 (95% 63.34, 77.49) | 0.713 (95% 64.38, 78.23) |
| 0.8 | 0.687 (95% 61.53, 75.83) | 0.619 (95% 54.19, 69.6) | 0.73 (95% 66.6, 79.32) | 0.736 (95% 67.4, 79.8) |
| 0.9 | 0.676 (95% 60.62, 74.59) | 0.621 (95% 54.61, 69.5) | 0.725 (95% 66.17, 78.75) | 0.731 (95% 66.98, 79.29) |
| 1 | 0.689 (95% 62.38, 75.36) | 0.609 (95% 53.62, 68.26) | 0.735 (95% 67.49, 79.41) | 0.743 (95% 68.42, 80.09) |
| 1.1 | 0.679 (95% 61.39, 74.34) | 0.603 (95% 52.96, 67.58) | 0.725 (95% 66.42, 78.49) | 0.733 (95% 67.34, 79.19) |
| 1.2 | 0.678 (95% 61.69, 73.98) | 0.605 (95% 53.6, 67.31) | 0.728 (95% 66.97, 78.56) | 0.735 (95% 67.76, 79.17) |
| 1.3 | 0.682 (95% 62.12, 74.32) | 0.608 (95% 53.96, 67.59) | 0.728 (95% 67.03, 78.64) | 0.735 (95% 67.81, 79.24) |
| 1.4 | 0.692 (95% 63.3, 75.14) | 0.612 (95% 54.54, 67.83) | 0.734 (95% 67.77, 79.06) | 0.74 (95% 68.45, 79.58) |
| 1.5 | 0.68 (95% 62.14, 73.95) | 0.631 (95% 56.58, 69.55) | 0.738 (95% 68.36, 79.32) | 0.744 (95% 69.01, 79.88) |
| 1.6 | 0.677 (95% 61.95, 73.44) | 0.615 (95% 55.27, 67.8) | 0.719 (95% 66.35, 77.4) | 0.722 (95% 66.64, 77.69) |
| 1.7 | 0.677 (95% 61.97, 73.36) | 0.622 (95% 55.89, 68.42) | 0.728 (95% 67.45, 78.19) | 0.734 (95% 68.03, 78.73) |
| 1.8 | 0.686 (95% 63.01, 74.25) | 0.628 (95% 56.66, 68.99) | 0.739 (95% 68.62, 79.1) | 0.743 (95% 69.06, 79.5) |
| 1.9 | 0.669 (95% 61.12, 72.61) | 0.645 (95% 58.44, 70.58) | 0.738 (95% 68.56, 79.03) | 0.744 (95% 69.19, 79.61) |
| 2 | 0.675 (95% 61.73, 73.27) | 0.649 (95% 58.79, 70.93) | 0.739 (95% 68.68, 79.19) | 0.745 (95% 69.22, 79.69) |
| 2.1 | 0.678 (95% 62, 73.67) | 0.647 (95% 58.57, 70.83) | 0.742 (95% 68.89, 79.5) | 0.746 (95% 69.28, 79.86) |
| 2.2 | 0.661 (95% 60.13, 72.16) | 0.65 (95% 58.74, 71.19) | 0.732 (95% 67.71, 78.71) | 0.738 (95% 68.31, 79.26) |
| 2.3 | 0.665 (95% 60.49, 72.6) | 0.646 (95% 58.33, 70.8) | 0.737 (95% 68.26, 79.17) | 0.742 (95% 68.73, 79.59) |

TABLE 3-continued

Areas under the curve (AUC) and confidence intervals for mortality. The competing risk models evaluated for mortality are summarized as follows: GAP index (GAP score), Genomic (high vs low risk profile), GAP index + Genomic (GAP score + high vs low risk profile), G-GAP index (GAP score + three additional points for high risk profile)

| Years | GAP Index only | Genomic only | GAP + genomic | G-GAP index |
|---|---|---|---|---|
| 2.4 | 0.665 | 0.628 | 0.723 | 0.726 |
|  | (95% 60.32, 72.69) | (95% 56.49, 69.19) | (95% 66.52, 78.03) | (95% 66.82, 78.31) |
| 2.5 | 0.68 | 0.627 | 0.734 | 0.735 |
|  | (95% 61.76, 74.16) | (95% 56.3, 69.15) | (95% 67.62, 79.14) | (95% 67.79, 79.31) |
| 2.6 | 0.689 | 0.63 | 0.739 | 0.741 |
|  | (95% 62.69, 75.04) | (95% 56.47, 69.44) | (95% 68.16, 79.66) | (95% 68.36, 79.84) |
| 2.7 | 0.671 | 0.621 | 0.726 | 0.728 |
|  | (95% 60.65, 73.61) | (95% 55.5, 68.77) | (95% 66.56, 78.73) | (95% 66.76, 78.92) |
| 2.8 | 0.682 | 0.624 | 0.735 | 0.737 |
|  | (95% 61.66, 74.81) | (95% 55.58, 69.17) | (95% 67.33, 79.66) | (95% 67.57, 79.87) |
| 2.9 | 0.68 | 0.623 | 0.735 | 0.738 |
|  | (95% 61.27, 74.65) | (95% 55.43, 69.17) | (95% 67.24, 79.73) | (95% 67.58, 80) |

TABLE 4

Areas under the curve (AUC) and confidence intervals for TFS. The CoxPH models evaluated for TFS are summarized as follows GAP index (GAP score), Genomic (high vs low risk profile), GAP index + Genomic (GAP score + high vs low risk profile), G-GAP index (GAP score + three additional points for high risk profile)

| Years | GAP Only | Genomic only | GAP + genomic | G-GAP |
|---|---|---|---|---|
| 0.1 | 0.7 | 0.725 | 0.794 | 0.806 |
|  | (95% 55.55-84.55) | (95% 62.67-82.24) | (95% 69.7-89.15) | (95% 71.71-89.43) |
| 0.2 | 0.709 | 0.662 | 0.76 | 0.768 |
|  | (95% 60.57-81.23) | (95% 57.64-74.74) | (95% 67.23-84.7) | (95% 68.51-85.11) |
| 0.3 | 0.661 | 0.674 | 0.733 | 0.74 |
|  | (95% 57.03-75.19) | (95% 60.12-74.7) | (95% 65.61-80.96) | (95% 66.52-81.56) |
| 0.4 | 0.65 | 0.668 | 0.726 | 0.736 |
|  | (95% 56.61-73.29) | (95% 59.9-73.74) | (95% 65.55-79.74) | (95% 66.63-80.52) |
| 0.5 | 0.654 | 0.641 | 0.717 | 0.724 |
|  | (95% 57.67-73.17) | (95% 57.04-71.13) | (95% 65-78.5) | (95% 65.69-79.03) |
| 0.6 | 0.673 | 0.621 | 0.723 | 0.727 |
|  | (95% 60.37-74.27) | (95% 55.1-69.16) | (95% 66.27-78.32) | (95% 66.74-78.67) |
| 0.7 | 0.656 | 0.618 | 0.709 | 0.713 |
|  | (95% 59-72.17) | (95% 55-68.62) | (95% 65.11-76.74) | (95% 65.6-77.09) |
| 0.8 | 0.688 | 0.622 | 0.735 | 0.736 |
|  | (95% 62.7-74.88) | (95% 55.74-68.64) | (95% 68.15-78.78) | (95% 68.37-78.89) |
| 0.9 | 0.687 | 0.612 | 0.732 | 0.733 |
|  | (95% 62.79-74.58) | (95% 54.71-67.72) | (95% 67.91-78.45) | (95% 68.09-78.55) |
| 1 | 0.701 | 0.613 | 0.747 | 0.747 |
|  | (95% 64.5-75.68) | (95% 55.01-67.52) | (95% 69.64-79.69) | (95% 69.75-79.74) |
| 1.1 | 0.698 | 0.607 | 0.741 | 0.742 |
|  | (95% 64.24-75.35) | (95% 54.5-67) | (95% 69.04-79.16) | (95% 69.2-79.25) |
| 1.2 | 0.703 | 0.612 | 0.748 | 0.751 |
|  | (95% 64.92-75.65) | (95% 55.05-67.25) | (95% 69.88-79.74) | (95% 70.16-79.95) |
| 1.3 | 0.706 | 0.614 | 0.749 | 0.752 |
|  | (95% 65.19-75.94) | (95% 55.33-67.52) | (95% 69.93-79.87) | (95% 70.31-80.13) |
| 1.4 | 0.715 | 0.616 | 0.751 | 0.754 |
|  | (95% 66.23-76.8) | (95% 55.62-67.65) | (95% 70.19-80.07) | (95% 70.48-80.28) |
| 1.5 | 0.706 | 0.628 | 0.757 | 0.76 |
|  | (95% 65.34-75.96) | (95% 56.86-68.68) | (95% 70.79-80.54) | (95% 71.15-80.83) |
| 1.6 | 0.699 | 0.617 | 0.74 | 0.742 |
|  | (95% 64.58-75.17) | (95% 55.84-67.54) | (95% 68.97-78.99) | (95% 69.21-79.2) |
| 1.7 | 0.699 | 0.627 | 0.749 | 0.751 |
|  | (95% 64.54-75.18) | (95% 56.88-68.57) | (95% 69.9-79.81) | (95% 70.19-80.07) |
| 1.8 | 0.7 | 0.725 | 0.794 | 0.806 |
|  | (95% 55.55-84.55) | (95% 62.67-82.24) | (95% 69.7-89.15) | (95% 71.71-89.43) |
| 1.9 | 0.709 | 0.662 | 0.76 | 0.768 |
|  | (95% 60.57-81.23) | (95% 57.64-74.74) | (95% 67.23-84.7) | (95% 68.51-85.11) |
| 2 | 0.661 | 0.674 | 0.733 | 0.74 |
|  | (95% 57.03-75.19) | (95% 60.12-74.7) | (95% 65.61-80.96) | (95% 66.52-81.56) |
| 2.1 | 0.65 | 0.668 | 0.726 | 0.736 |
|  | (95% 56.61-73.29) | (95% 59.9-73.74) | (95% 65.55-79.74) | (95% 66.63-80.52) |
| 2.2 | 0.654 | 0.641 | 0.717 | 0.724 |
|  | (95% 57.67-73.17) | (95% 57.04-71.13) | (95% 65-78.5) | (95% 65.69-79.03) |
| 2.3 | 0.673 | 0.621 | 0.723 | 0.727 |
|  | (95% 60.37-74.27) | (95% 55.1-69.16) | (95% 66.27-78.32) | (95% 66.74-78.67) |

TABLE 4-continued

Areas under the curve (AUC) and confidence intervals for TFS. The CoxPH
models evaluated for TFS are summarized as follows GAP index (GAP score),
Genomic (high vs low risk profile), GAP index + Genomic (GAP score +
high vs low risk profile), G-GAP index (GAP score + three additional
points for high risk profile)

| Years | GAP Only | Genomic only | GAP + genomic | G-GAP |
|---|---|---|---|---|
| 2.4 | 0.656 | 0.618 | 0.709 | 0.713 |
|  | (95% 59-72.17) | (95% 55-68.62) | (95% 65.11-76.74) | (95% 65.6-77.09) |
| 2.5 | 0.688 | 0.622 | 0.735 | 0.736 |
|  | (95% 62.7-74.88) | (95% 55.74-68.64) | (95% 68.15-78.78) | (95% 68.37-78.89) |
| 2.6 | 0.687 | 0.612 | 0.732 | 0.733 |
|  | (95% 62.79-74.58) | (95% 54.71-67.72) | (95% 67.91-78.45) | (95% 68.09-78.55) |
| 2.7 | 0.701 | 0.613 | 0.747 | 0.747 |
|  | (95% 64.5-75.68) | (95% 55.01-67.52) | (95% 69.64-79.69) | (95% 69.75-79.74) |
| 2.8 | 0.698 | 0.607 | 0.741 | 0.742 |
|  | (95% 64.24-75.35) | (95% 54.5-67) | (95% 69.04-79.16) | (95% 69.2-79.25) |
| 2.9 | 0.703 | 0.612 | 0.748 | 0.751 |
|  | (95% 64.92-75.65) | (95% 55.05-67.25) | (95% 69.88-79.74) | (95% 70.16-79.95) |

TABLE 5

Results of CoxPH models to determine the association between
bidirectional changes in SAMS scores and transplant-free survival.
Results adjusted to age, gender, forced vital capacity and
immunosuppression use

| Month | P value | Hazard ratio | 95% Confidence interval |
|---|---|---|---|
| 1 | 0.025 | 3.18 | 1.16-8.76 |
| 2 | 0.249 | 1.71 | 0.686-4.27 |
| 3 | 0.206 | 1.8 | 0.724-4.46 |
| 4 | 0.114 | 1.98 | 0.85-4.59 |
| 5 | 0.144 | 1.91 | 0.801-4.55 |
| 6 | 0.129 | 1.99 | 0.818-4.86 |

TABLE 6

Details of anti-fibrotic therapy in the Yale time
course cohort

| 52-gene risk profiles | High risk | Low risk |
|---|---|---|
| Number of patients | 10 | 22 |
| Number of patients initiated on anti-fibrotic therapy during follow up | 9 | 16 |
| Number of patients on Pirfenidone/Nintedanib | 7/2 | 13/3 |

REFERENCES

The following references are cited in the sections above.
1. Raghu G, Chen S Y, Yeh W S, et al. Idiopathic pulmonary fibrosis in US Medicare beneficiaries aged 65 years and older: incidence, prevalence, and survival, 2001-11. Lancet Respir Med 2014; 2: 566-72.
2. Martinez F J, Safrin S, Weycker D, et al. The clinical course of patients with idiopathic pulmonary fibrosis. Ann Intern Med 2005; 142: 963-67.
3. Ley B, Ryerson C J, Vittinghoff E, et al. A multidimensional index and staging system for idiopathic pulmonary fibrosis. Ann Intern Med 2012; 156: 684-91.
4. Richards T J, Kaminski N, Baribaud F, et al. Peripheral blood proteins predict mortality in idiopathic pulmonary fibrosis. Am J Respir Crit Care Med 2012; 185: 67-76.
5. Greene K E, King T E Jr, Kuroki Y, et al. Serum surfactant proteins-A and -D as biomarkers in idiopathic pulmonary fibrosis. Eur Respir J 2002; 19: 439-46.
6. Herazo-Maya J D, Noth I, Duncan S R, et al. Peripheral blood mononuclear cell gene expression profiles predict poor outcome in idiopathic pulmonary fibrosis. Sci Transl Med 2013; 5: 205ra136.
7. Peljto A L, Zhang Y, Fingerlin T E, et al. Association between the MUC5B promoter polymorphism and survival in patients with idiopathic pulmonary fibrosis. JAMA 2013; 309: 2232-39.
8. Stuart B D, Lee J S, Kozlitina J, et al. Effect of telomere length on survival in patients with idiopathic pulmonary fibrosis: an observational cohort study with independent validation. Lancet Respir Med 2014; 2: 557-65.
9. Ley B, Brown K K, Collard H R. Molecular biomarkers in idiopathic pulmonary fibrosis. Am J Physiol Lung Cell Mol Physiol 2014; 307: L681-91.
10. Raghu G, Collard H R, Egan J J, et al. An official ATS/ERS/JRS/ALAT statement: idiopathic pulmonary fibrosis: evidence-based guidelines for diagnosis and management. Am J Respir Crit Care Med 2011; 183: 788-824.
11. Geiss G K, Bumgarner R E, Birditt B, et al. Direct multiplexed measurement of gene expression with color-coded probe pairs. Nat Biotechnol 2008; 26: 317-25.
12. Molyneaux P L, Willis-Owen S A G, Cox M J, et al. Host-microbial interactions in idiopathic pulmonary fibrosis. Am J Respir Crit Care Med 2017; 195: 1640-50.
13. Tzouvelekis A, Herazo-Maya J D, Slade M, et al. Validation of the prognostic value of MMP-7 in idiopathic pulmonary fibrosis. Respirology 2017; 22: 486-93.
14. Rosas I O, Richards T J, Konishi K, et al. MMP1 and MMP7 as potential peripheral blood biomarkers in idiopathic pulmonary fibrosis. PLoS Med 2008; 5: e93.
15. Fine J P G R. A proportional hazards model for the subdistribution of a competing risk. J Am Stat Assoc 1999; 94: 496-509.
16. Therneau T M, Grambsch P M. Modeling survival data: extending the Cox model. New York, N.Y.: Springer; 2000.
17. Heagerty P J, Lumley T, Pepe M S. Time-dependent ROC curves for censored survival data and a diagnostic marker. Biometrics 2000; 56: 337-44.
18. Harrell F E Jr, Lee K L, Mark D B. Multivariable prognostic models: issues in developing models, evaluating assumptions and adequacy, and measuring and reducing errors. Stat Med 1996; 15: 361-87.

19. Bates D, Machler M, Bolker B, Walker S. Fitting linear mixed-effects models using lme4. J Stat Softw 2015; 67: 1-48.
20. Idiopathic Pulmonary Fibrosis Clinical Research Network, Raghu G, Anstrom K J, King T E Jr, Lasky J A, Martinez F J. Prednisone, azathioprine, and N-acetylcysteine for pulmonary fibrosis. N Engl J Med 2012; 366: 1968-77.
21. Richeldi L, Ryerson C J, Lee J S, et al. Relative versus absolute change in forced vital capacity in idiopathic pulmonary fibrosis. Thorax 2012; 67: 407-11.
22. du Bois R M, Weycker D, Albera C, et al. Forced vital capacity in patients with idiopathic pulmonary fibrosis: test properties and minimal clinically important difference. Am J Respir Critic Care Med 2011; 184: 1382-89.
23. Yokoyama A, Kondo K, Nakajima M, et al. Prognostic value of circulating KL-6 in idiopathic pulmonary fibrosis. Respirology 2006; 11: 164-68.
24. Prasse A, Probst C, Bargagli E, et al. Serum CC-chemokine ligand 18 concentration predicts outcome in idiopathic pulmonary fibrosis. Am J Respir Critic Care Med 2009; 179: 717-23.
25. Korthagen N M, van Moorsel C H, Barlo N P, et al. Serum and BALF YKL-40 levels are predictors of survival in idiopathic pulmonary fibrosis. Respir Med 2011; 105: 106-13.
26. Vuga L J, Tedrow J R, Pandit K V, et al. C-X-C motif chemokine 13 (CXCL13) is a prognostic biomarker of idiopathic pulmonary fibrosis. Am J Respir Critic Care Med 2014; 189: 966-74.
27. Tajiri M, Okamoto M, Fujimoto K, et al. Serum level of periostin can predict long-term outcome of idiopathic pulmonary fibrosis. Respir Investig 2015; 53: 73-81.
28. Kahloon R A, Xue J, Bhargava A, et al. Patients with idiopathic pulmonary fibrosis with antibodies to heat shock protein 70 have poor prognoses. Am J Respir Critic Care Med 2013; 187: 768-75.
29. Jenkins R G, Simpson J K, Saini G, et al. Longitudinal change in collagen degradation biomarkers in idiopathic pulmonary fibrosis: an analysis from the prospective, multicentre PROFILE study. Lancet Respir Med 2015; 3: 462-72.
30. Moeller A, Gilpin S E, Ask K, et al. Circulating fibrocytes are an indicator of poor prognosis in idiopathic pulmonary fibrosis. Am J Respir Critic Care Med 2009; 179: 588-94.
31. Reilkoff R A, Peng H, Murray L A, et al. Semaphorin 7a+ regulatory T cells are associated with progressive idiopathic pulmonary fibrosis and are implicated in transforming growth factor-beta1-induced pulmonary fibrosis. Am J Respir Critic Care Med 2013; 187: 180-88.
32. Noth I, Zhang Y, Ma S F, et al. Genetic variants associated with idiopathic pulmonary fibrosis susceptibility and mortality: a genome-wide association study. Lancet Respir Med 2013; 1: 309-17.
33. O'Dwyer D N, Armstrong M E, Trujillo G, et al. The Toll-like receptor 3 L412F polymorphism and disease progression in idiopathic pulmonary fibrosis. Am J Respir Critic Care Med 2013; 188: 1442-50.
34. Ryu C, Sun H, Gulati M, et al. Extracellular mitochondrial DNA is generated by fibroblasts and predicts death in idiopathic pulmonary fibrosis. Am J Respir Critic Care Med 2017; published online August 7. DOI:10.1164/rccm.201612-2480OC.
35. Lindell K O, Liang Z, Hoffman L A, et al. Palliative care and location of death in decedents with idiopathic pulmonary fibrosis. Chest 2015; 147: 423-29.
36. Gilani S R, Vuga L J, Lindell K O, et al. CD28 down-regulation on circulating CD4 T-cells is associated with poor prognoses of patients with idiopathic pulmonary fibrosis. PLoS One 2010; 5: e8959.
37. McKinney E F, Lee J C, Jayne D R, Lyons P A, Smith K G. T-cell exhaustion, co-stimulation and clinical outcome in autoimmunity and infection. Nature 2015; 523: 612-16.
38. Li K, Wang S W, Li Y, et al. Identification and expression of a new type II transmembrane protein in human mast cells. Genomics 2005; 86: 68-75.
39. Wygrecka M, Dahal B K, Kosanovic D, et al. Mast cells and ibroblasts work in concert to aggravate pulmonary fibrosis: role of transmembrane SCF and the PAR-2/PKC-alpha/Raf-1/p44/42 signaling pathway. Am J Pathol 2013; 182: 2094-108.
40. Jylhä M, Paavilainen P, Lehtimäki T, et al. Interleukin-1 receptor antagonist, interleukin-6, and C-reactive protein as predictors of mortality in nonagenarians: the vitality 90+ study. J Gerontol A Biol Sci Med Sci 2007; 62: 1016-21.
41. Jylhava J, Raitanen J, Marttila S, Hervonen A, Jylha M, Hurme M. Identification of a prognostic signature for old-age mortality by integrating genome-wide transcriptomic data with the conventional predictors: the Vitality 90+ Study. BMC Med Genomics 2014; 7: 54.

What is claimed is:

1. A method of assessing a blood sample obtained from an individual, the method comprising:
  (a) obtaining RNA from a blood sample from an individual;
  (b) combining the RNA obtained in (a) with nucleic acid probes that hybridize to at least one of the following 52 genes: PLBD1, TPST1, C19orf59 (MCEMP1), IL1R2, HP, FLT3, S100A12, LCK, CAMK2D, NUP43, SLAMF7, LRRC39, ICOS, CD47, LBH, SH2D1A, CNOT6L, METTL8, ETS1, C2orf27A, P2RY10, TRAT1, BTN3A1, LARP4, TC2N, GPR183, MORC4, STAT4, LPAR6, C7orf58 (CPED1), DOCK10, ARHGAP5, HLA-DPA1, BIRC3, GPR174, CD28, UTRN, CD2, HLA-DPB1, ARL4C, BTN3A3, CXCR6, DYNC2LI1, BTN3A2, ITK, SNHG1, CD96, GBP4, S1PR1, NAP1L2, KLF12, and IL7R, thereby producing a combination;
  (c) maintaining the combination under conditions under which hybridization of RNA and nucleic acid probes occurs, thereby producing RNA-nucleic acid probe complexes;
  (d) measuring the number of RNA-nucleic acid probe complexes for each of the 52 genes;
  (e) producing an expression level for each of the genes based on the number of RNA-nucleic acid probe complexes measured in (d);
  (f) comparing the expression level of each gene with a gene-specific reference value, thereby producing a normalized expression level for each gene;
  (g) determining (i) if the normalized expression level of each of PLBD1, TPST1, C19orf59 (MCEMP1), IL1R2, HP, FLT3, and S100A12 is greater than the gene-specific reference value, wherein if the normalized expression level of a gene in the sample is greater than the gene-specific reference value, the gene is an upregulated gene and (ii) if the normalized expression level of each of LCK, CAMK2D, NUP43, SLAMF7, LRRC39, ICOS, CD47, LBH, SH2D1A, CNOT6L, METTL8, ETS1, C2orf27A, P2RY10, TRAT1, BTN3A1, LARP4, TC2N, GPR183, MORC4, STAT4, LPAR6, C7orf58 (CPED1), DOCK10, ARHGAP5, HLA-DPA1, BIRC3, GPR174, CD28, UTRN, CD2, HLA-DPB1, ARL4C, BTN3A3, CXCR6, DYNC2LI1, BTN3A2, ITK, SNHG1, CD96, GBP4, S1PR1, NAP1L2, KLF12, and IL7R is less than the gene-specific standard, wherein if the normalized expression level of a gene in the sample is less than the gene-specific standard, the gene is a downregulated gene;

(h) calculating (i) the proportion of upregulated genes in the sample, thereby producing a proportion of upregulated genes and (ii) the proportion of downregulated genes in the sample, thereby producing a proportion of downregulated genes;

(i) adding the normalized expression levels of the upregulated genes and multiplying the resulting sum by the proportion of upregulated genes calculated in (h)(i), thereby producing an up score;

(j) adding the normalized expression levels of the downregulated genes and multiplying the resulting sum by the proportion of downregulated genes calculated in (h)(ii), thereby producing a down score; and (k) comparing the up score to a reference median up score and the down score to a reference median down score.

2. The method of claim 1, wherein the individual has idiopathic pulmonary fibrosis.

3. The method of claim 2, wherein, if the up score is equal to or greater than the reference median up score and the down score is equal to or less than the reference median down score, the individual is at a greater risk of poor disease outcome compared to an individual in whom the up score is less than the reference median up score and the down score is greater than the reference median down score.

4. The method of claim 3, wherein the poor disease outcome is death or a shortened period of transplant-free survival.

5. The method of claim 1, wherein the expression level of each of the 52 genes is measured by gene transcript count.

6. The method of claim 1, further comprising use of the gender, age, and physiology (GAP) index for idiopathic pulmonary fibrosis mortality.

7. The method of claim 1, wherein the sample is mononuclear cells or RNA obtained therefrom.

8. The method of claim 5, wherein the gene transcript count is carried out using the Nanostring preparation station and digital analyzer.

9. The method of claim 1, further comprising:

(l) repeating steps (a) through (k) in a blood sample obtained from the individual at a later time, thereby producing a second up score and a second down score;

(m) calculating the difference between the up score of (i) and the second up score;

(n) calculating the difference between the down score of (j) and the second down score; and (o) determining whether the second up score is at least 10% greater than the up score of (i) and whether the second down score is at least 10% lower than the down score of (j), wherein, if the second up score is at least 10% greater than the up score of (i) and the second down score is at least 10% lower than the down score of (j), the individual is at high risk of poor disease outcome and if one or none of the changes in/up score and in down score are less than 10%, the individual is at low risk of poor disease outcome.

10. The method of claim 9, further comprising use of the GAP index for idiopathic pulmonary fibrosis mortality.

11. The method of claim 9, wherein the sample is mononuclear cells or RNA obtained therefrom.

12. The method of claim 9, wherein the gene transcript count is carried out using the Nanostring preparation station and digital analyzer.

13. The method of claim 1, wherein the reference population is individuals diagnosed with idiopathic pulmonary fibrosis.

14. The method of claim 1, wherein the measuring the gene transcript count is carried out using gene expression microarray analysis.

15. The method of claim 1, wherein the reference median up score comprises the median calculated from up score in a reference population, and wherein the reference population comprises individuals diagnosed with idiopathic pulmonary fibrosis.

16. The method of claim 1, wherein the reference median down score comprises the median calculated from down score in a reference population, and wherein the reference population comprises individuals diagnosed with idiopathic pulmonary fibrosis.

17. The method of claim 1, wherein the sample comprises peripheral blood mononuclear cells.

18. The method of claim 9, wherein the sample comprises peripheral blood mononuclear cells.

19. The method of claim 1, wherein the gene-specific reference value is the geometric mean for the gene in a reference population.

20. The method of claim 19, wherein the reference population is individuals diagnosed with idiopathic pulmonary fibrosis.

* * * * *